(12) United States Patent
Salk et al.

(10) Patent No.: US 12,258,629 B2
(45) Date of Patent: *Mar. 25, 2025

(54) METHODS OF LOWERING THE ERROR RATE OF MASSIVELY PARALLEL DNA SEQUENCING USING DUPLEX CONSENSUS SEQUENCING

(71) Applicant: UNIVERSITY OF WASHINGTON THROUGH ITS CENTER FOR COMMERCIALIZATION, Seattle, WA (US)

(72) Inventors: Jesse Salk, Seattle, WA (US); Lawrence A. Loeb, Bellevue, WA (US); Michael Schmitt, Seattle, WA (US)

(73) Assignee: UNIVERSITY OF WASHINGTON THROUGH ITS CENTER FOR COMMERCIALIZATION, Seattle, WA (US)

( * ) Notice: Subject to any disclaimer, the term of this patent is extended or adjusted under 35 U.S.C. 154(b) by 0 days.

This patent is subject to a terminal disclaimer.

(21) Appl. No.: 16/503,398

(22) Filed: Jul. 3, 2019

(65) Prior Publication Data
US 2019/0352714 A1 Nov. 21, 2019

Related U.S. Application Data

(63) Continuation of application No. 16/120,072, filed on Aug. 31, 2018, now Pat. No. 10,385,393, which is a continuation of application No. 15/660,785, filed on Jul. 26, 2017, now Pat. No. 10,287,631, which is a continuation of application No. 14/386,800, filed as application No. PCT/US2013/032665 on Mar. 15, 2013, now Pat. No. 9,752,188.

(60) Provisional application No. 61/625,319, filed on Apr. 17, 2012, provisional application No. 61/625,623, filed on Apr. 17, 2012, provisional application No. 61/613,413, filed on Mar. 20, 2012.

(51) Int. Cl.
| | | |
|---|---|---|
| C12Q 1/68 | (2018.01) | |
| C12Q 1/6806 | (2018.01) | |
| C12Q 1/6869 | (2018.01) | |
| C12Q 1/6876 | (2018.01) | |

(52) U.S. Cl.
CPC ......... C12Q 1/6876 (2013.01); C12Q 1/6806 (2013.01); C12Q 1/6869 (2013.01)

(58) Field of Classification Search
CPC ... C12Q 1/6876; C12Q 1/6806; C12Q 1/6869
See application file for complete search history.

(56) References Cited

U.S. PATENT DOCUMENTS

| | | |
|---|---|---|
| 5,308,751 A | 5/1994 | Ohkawa et al. |
| 6,251,610 B1 | 6/2001 | Gupte et al. |
| 6,498,023 B1 | 12/2002 | Abarzua |
| 6,582,908 B2 | 6/2003 | Fodor et al. |
| 6,958,225 B2 | 10/2005 | Dong |
| 7,214,490 B2 | 5/2007 | Su et al. |
| 7,267,966 B2 | 9/2007 | Dong et al. |
| 7,297,778 B2 | 11/2007 | Matsuzaki et al. |
| 7,406,385 B2 | 7/2008 | Sorenson |
| 7,452,699 B2 | 11/2008 | Makrigiorgos et al. |
| 7,459,273 B2 | 12/2008 | Jones et al. |
| 7,476,503 B2 | 1/2009 | Turner et al. |
| 7,741,463 B2 | 6/2010 | Gormley et al. |
| 7,754,429 B2 | 7/2010 | Rigatti |
| 8,029,993 B2 | 10/2011 | Mikawa |
| 8,148,068 B2 | 4/2012 | Brenner et al. |
| 8,153,375 B2 | 4/2012 | Travers et al. |

(Continued)

FOREIGN PATENT DOCUMENTS

| | | |
|---|---|---|
| EP | 2893040 B1 | 2/2019 |
| WO | 2006113422 A2 | 10/2006 |

(Continued)

OTHER PUBLICATIONS

Kinde et al. (PNAS, 2011, 108(23):9530-9535, cited in IDS) (Year: 2011).*
Travers et al. Nucleic Acids Reserach, 2010, 38(15):e159, pp. 1-8 (Year: 2010)*
Ameur A, Stewart JB, Freyer C, Hagstrom E, Ingman M, Larsson N-G, et al. UltraDeep Sequencing of Mouse Mitochondrial DNA: Mutational Patterns and Their Origins. PLoS Genet. 2011;7:e1 002028.
Bainbridge MN, Wang M, Burgess DL, Kovar C, Rodesch M, D'Ascenzo M, et al. Whole exome capture in solution with 3 Gbp of data. Genome Bioi. 2010;11: R62:1-8.

(Continued)

Primary Examiner — Stephanie K Mummert
(74) Attorney, Agent, or Firm — Perkins Coie LLP

(57) ABSTRACT

Next Generation DNA sequencing promises to revolutionize clinical medicine and basic research. However, while this technology has the capacity to generate hundreds of billions of nucleotides of DNA sequence in a single experiment, the error rate of approximately 1% results in hundreds of millions of sequencing mistakes. These scattered errors can be tolerated in some applications but become extremely problematic when "deep sequencing" genetically heterogeneous mixtures, such as tumors or mixed microbial populations. To overcome limitations in sequencing accuracy, a method Duplex Consensus Sequencing (DCS) is provided. This approach greatly reduces errors by independently tagging and sequencing each of the two strands of a DNA duplex. As the two strands are complementary, true mutations are found at the same position in both strands. In contrast, PCR or sequencing errors will result in errors in only one strand. This method uniquely capitalizes on the redundant information stored in double-stranded DNA, thus overcoming technical limitations of prior methods utilizing data from only one of the two strands.

34 Claims, 12 Drawing Sheets

Specification includes a Sequence Listing.

(56) References Cited

U.S. PATENT DOCUMENTS

| | | |
|---|---|---|
| 8,318,434 B2 | 11/2012 | Cuppens |
| 8,715,967 B2 | 5/2014 | Casbon et al. |
| 8,732,064 B2 | 5/2014 | Micklem et al. |
| 8,741,606 B2 | 6/2014 | Casbon et al. |
| 9,080,210 B2 | 7/2015 | Van Eijk et al. |
| 9,085,798 B2 | 7/2015 | Chee |
| 9,249,460 B2 | 2/2016 | Pushkarev et al. |
| 9,260,753 B2 | 2/2016 | Xie et al. |
| 9,476,095 B2 | 10/2016 | Vogelstein et al. |
| 9,598,731 B2 | 3/2017 | Talasaz |
| 9,745,627 B2 | 8/2017 | Van Eijk et al. |
| 9,752,188 B2 | 9/2017 | Schmitt et al. |
| 9,783,847 B2 | 10/2017 | Chee |
| 9,834,822 B2 | 12/2017 | Talasaz |
| 9,862,995 B2 | 1/2018 | Patel |
| 9,898,577 B2 | 2/2018 | Van Eijk et al. |
| 9,920,366 B2 | 3/2018 | Eltoukhy et al. |
| 10,000,800 B2 | 6/2018 | Chee |
| 10,011,871 B2 | 7/2018 | Bielas |
| 10,023,907 B2 | 7/2018 | Van Eijk et al. |
| 10,119,165 B2 | 11/2018 | Chee |
| 10,202,646 B2 | 2/2019 | Fodor et al. |
| 10,266,883 B2 | 4/2019 | Chee |
| 10,266,884 B2 | 4/2019 | Chee |
| 10,287,630 B2 | 5/2019 | Xie et al. |
| 10,287,631 B2 | 5/2019 | Salk et al. |
| 10,501,793 B2 | 12/2019 | Chee |
| 10,604,804 B2 | 3/2020 | Salk et al. |
| 10,689,699 B2 | 6/2020 | Salk et al. |
| 10,711,304 B2 * | 7/2020 | Salk ............... C12Q 1/6869 |
| 10,752,951 B2 | 8/2020 | Salk et al. |
| 10,760,127 B2 | 9/2020 | Salk et al. |
| 2003/0165923 A1 | 9/2003 | Li et al. |
| 2004/0209299 A1 | 10/2004 | Pinter et al. |
| 2005/0100900 A1 | 5/2005 | Kawashima et al. |
| 2007/0020640 A1 | 1/2007 | McCloskey et al. |
| 2007/0128624 A1 | 6/2007 | Gormley et al. |
| 2007/0172839 A1 | 7/2007 | Smith et al. |
| 2007/0172873 A1 | 7/2007 | Brenner et al. |
| 2008/0167195 A1 | 7/2008 | Li et al. |
| 2008/0261204 A1 | 10/2008 | Lexow |
| 2009/0093378 A1 | 4/2009 | Bignell |
| 2009/0233802 A1 | 9/2009 | Bignell et al. |
| 2009/0298075 A1 * | 12/2009 | Travers ............... C12Q 1/6855 435/6.12 |
| 2010/0069263 A1 | 3/2010 | Shendure et al. |
| 2010/0222238 A1 | 9/2010 | Smith et al. |
| 2011/0160078 A1 | 6/2011 | Fodor et al. |
| 2011/0301042 A1 | 12/2011 | Steinmann et al. |
| 2012/0058468 A1 | 3/2012 | McKeown |
| 2012/0071331 A1 | 3/2012 | Casbon et al. |
| 2012/0094847 A1 | 4/2012 | Warthmann et al. |
| 2012/0165202 A1 | 6/2012 | Porreca et al. |
| 2012/0208724 A1 | 8/2012 | Steemers et al. |
| 2012/0220494 A1 | 8/2012 | Samuels et al. |
| 2012/0238738 A1 | 9/2012 | Hendrickson et al. |
| 2012/0244525 A1 | 9/2012 | Hendrickson |
| 2012/0322666 A1 | 12/2012 | Pham et al. |
| 2013/0116417 A1 | 5/2013 | Krauss et al. |
| 2014/0057799 A1 | 2/2014 | Johnson et al. |
| 2014/0134610 A1 | 5/2014 | Pham et al. |
| 2014/0155274 A1 * | 6/2014 | Xie ............... C12Q 1/6853 506/2 |
| 2014/0329282 A1 | 11/2014 | Nelson et al. |
| 2014/0329698 A1 | 11/2014 | Bignell et al. |
| 2015/0024950 A1 * | 1/2015 | Bielas ............... C12N 15/1065 506/4 |
| 2015/0299812 A1 | 10/2015 | Talasaz |
| 2016/0026758 A1 | 1/2016 | Jabara et al. |
| 2016/0319345 A1 | 11/2016 | Gnerre et al. |
| 2017/0247687 A1 * | 8/2017 | Shendure ............ C12Q 1/6874 |
| 2018/0023135 A1 | 1/2018 | Van Eijk et al. |
| 2018/0363048 A1 | 12/2018 | Bielas |
| 2018/0363049 A1 | 12/2018 | Bielas |
| 2018/0363051 A1 | 12/2018 | Salk et al. |
| 2018/0363052 A1 | 12/2018 | Salk et al. |
| 2018/0363053 A1 | 12/2018 | Salk et al. |
| 2019/0093160 A1 | 3/2019 | Salk et al. |
| 2019/0093161 A1 | 3/2019 | Salk et al. |
| 2019/0093162 A1 | 3/2019 | Salk et al. |
| 2019/0119748 A1 | 4/2019 | Salk et al. |
| 2019/0119749 A1 | 4/2019 | Salk et al. |
| 2019/0177803 A1 | 6/2019 | Talasaz |
| 2019/0271040 A1 | 9/2019 | Salk et al. |
| 2019/0284626 A1 | 9/2019 | Salk et al. |
| 2019/0284627 A1 | 9/2019 | Salk et al. |
| 2019/0292597 A1 | 9/2019 | Salk et al. |
| 2019/0323082 A1 | 10/2019 | Salk et al. |
| 2019/0338358 A1 | 11/2019 | Salk et al. |
| 2020/0048701 A1 | 2/2020 | Chee |
| 2020/0048702 A1 | 2/2020 | Chee |
| 2020/0048703 A1 | 2/2020 | Chee |
| 2020/0087736 A1 | 3/2020 | Talasaz |
| 2020/0115746 A1 | 4/2020 | Talasaz |
| 2020/0318185 A1 | 10/2020 | Salk et al. |
| 2020/0392580 A1 | 12/2020 | Salk et al. |
| 2021/0277467 A1 | 9/2021 | Vogelstein |
| 2021/0324470 A1 | 10/2021 | Salk et al. |
| 2021/0371920 A1 | 12/2021 | Salk et al. |
| 2021/0371921 A1 | 12/2021 | Salk et al. |
| 2021/0371922 A1 | 12/2021 | Salk et al. |
| 2021/0371923 A1 | 12/2021 | Salk et al. |
| 2021/0371924 A1 | 12/2021 | Salk et al. |
| 2021/0381048 A1 | 12/2021 | Salk et al. |
| 2022/0010376 A1 | 1/2022 | Salk et al. |
| 2022/0017961 A1 | 1/2022 | Salk et al. |
| 2022/0195523 A1 | 6/2022 | Salk et al. |
| 2022/0290231 A1 | 9/2022 | Salk et al. |
| 2024/0035088 A1 | 2/2024 | Salk et al. |
| 2024/0084385 A1 | 3/2024 | Salk et al. |

FOREIGN PATENT DOCUMENTS

| | | | |
|---|---|---|---|
| WO | 2011021102 A2 | 2/2011 | |
| WO | 2012042374 A2 | 4/2012 | |
| WO | 2012061832 A1 | 5/2012 | |
| WO | 2012129363 A2 | 9/2012 | |
| WO | WO-2013123442 A1 * | 8/2013 | ............ C12N 15/10 |
| WO | 2013142389 A1 | 9/2013 | |
| WO | 2015100427 A1 | 7/2015 | |
| WO | 2017100441 A1 | 6/2017 | |

OTHER PUBLICATIONS

Boyd SO, Marshall EL, Merker JD, Maniar JM, Zhang LN, Sahaf B, et al. Measurement and Clinical Monitoring of Human Lymphocyte Clonality by Massively Parallel V-D-J Pyrosequencing. Science Translational Medicine. 2009;1 :12ra23-12ra23.

Campbell PJ, Pleasance ED, Stephens PJ, Dicks E, Rance R, Goodhead I, et al. Subclonal phylogenetic structures in cancer revealed by ultra-deep sequencing. Proc Natl Acad Sci USA. 2008; 105:13081-6.

Carlson CA, Kas A, Kirkwood R, Hays LE, Preston BD, Salipante SJ, et al. Decoding cell lineage from acquired mutations using arbitrary deep sequencing. Nat Methods. 2012;9:78-80.

Casbon JA, Osborne RJ, Brenner S, Lichtenstein CP. A method for counting PCR template molecules with application to next-generation sequencing. Nucleic Acids Research. 2011;39:e81-e.

Cervantes RB, Stringer JR, Shao C, Tischfield JA, Stambrook PJ. Embryonic stem cells and somatic cells differ in mutation frequency and type. Proc Natl Acad Sci USA. 2002;99:3586-90.

Chiu RWK, Akolekar R, Zheng YWL, Leung TY, Sun H, Chan KCA, et al. Noninvasive prenatal assessment of trisomy 21 by multiplexed maternal plasma DNA sequencing: large scale validity study. BMJ. 2011 ;342:c7401.

De Grassi A, Segala C, Iannelli F, Volorio S, Bertario L, Radice P, et al. Ultradeep Sequencing of a Human Ultraconserved Region Reveals Somatic and Constitutional Genomic Instability. PLoS Biol. 2010;8:e1000275.

Ding L, Ley T J, Larson DE, Miller CA, Koboldt DC, Welch JS, et al. Clonal evolution in relapsed acute myeloid leukaemia revealed by whole-genome sequencing. Nature. 21 05;481:506-9.

(56) References Cited

OTHER PUBLICATIONS

Druley TE, Vallania FLM, Wegner OJ, Varley KE, Knowles OL, Bonds JA, et al. Quantification of rare allelic variants from pooled genomic DNA. Nat Methods. 2009;6 :263-5.
Ehrich M, Deciu C, Zwiefelhofer T, Tynan JA, Cagasan L, Tim R, et al. Noninvasive detection of fetal trisomy 21 by sequencing of DNA in maternal blood: a study in a clinical setting. Am J Obsbet Gynecol. 2011;204:205e1-11.
European Patent Office, Extended European Search Report for EP13764186.6, dated Sep. 8, 2015, 3 pages.
European Patent Office, Examination Report for EP13764186.6, dated May 13, 2016, 6 pages.
European Patent Office, Examination Report for EP13764186.6, dated Jan. 31, 2017, 7 pages.
European Patent Office, Examination Report for EP13764186.6, dated Aug. 10, 2017, 7 pages.
European Patent Office, Examination Report for EP13764186.6, dated Jun. 8, 2018, 5 pages.
European Patent Office, Examination Report for EP13764186.6, dated Oct. 4, 2018, 6 pages.
Fan HC, Blumenfeld YJ, Chitkara U, Hudgins L, Quake Sr. Noninvasive diagnosis of fetal aneuploidy by shotgun sequencing DNA from maternal blood. Proc Natl Acad Sci USA. 2008;105:16266-71.
Flaherty P, Natsoulis G, Muralidharan O, Winters M, Buenrostro J, Bell J, et al. Ultrasensitive detection of rare mutations using next-generation targeted resequencing. Nucleic Acids Research. 2012;40:e2-e.
Fordyce SL, Avila-Areas MC, Rockenbauer E, B0rsting C, Frank-Hansen R, Petersen FT, et al. High-throughput sequencing of core STR loci for forensic genetic investigations using the Roche Genome Sequencer FLX platform. BioTechniques. 2011;51 :127-33.
Fu GK, Hu J, Wang P-H, Fodor SPA. Counting individual DNA molecules by the stochastic attachment of diverse labels. Proc Natl Acad Sci USA. 2011;108:9026-31.
Garcia-Garcera M, Gigli E, Sanchez-Quinto F, Ramirez O, Calafell F, Civit S, et al. Fragmentation of contaminant and endogenous DNA in ancient samples determined by shotgun sequencing; prospects for human palaeogenomics. PLoS ONE. 2011;6:e24161.
Greaves LC, et al. (2009) Quantification of mitochondrial DNA mutation load. Aging Cell 8:566-572.
Haag-Liautard C, et al. (2008) Direct estimation of the mitochondrial DNA mutation rate in *Drosophila melanogaster*. PLoS Bioi 6:e204.
He Y, Wu J, Dressman DC, Iacobuzio-Donahue C, Markowitz SD, Velculescu VE, et al. Heteroplasmic mitochondrial DNA mutations in normal and tumour cells. Nature. 2010;464:610-4.
Howell N, Kubacka I, Mackey DA (1996) How rapidly does the human mitochondrial genome evolve? Am J Hum Genet 59:501-509.
Hyman RW, Herndon CN, Jiang H, Palm C, Fukushima M, Bernstein D, et al. The dynamics of the vaginal microbiome during infertility therapy with in vitro fertilization embryo transfer. J Assist Reprod Genet. 2012;29:105-15.
Jabara CB, Jones CD, Roach J, Anderson JA, Swanstrom R. Accurate sampling and deep sequencing of the HIV-1 protease gene using a Primer ID. Proc Natl Acad Sci USA. 2011;108:20166-71.
Jazin EE, Cavelier L, Eriksson I, Oreland L, Gyllensten U (1996) Human brain contains high levels of heteroplasmy in the noncoding regions of mitochondrial DNA. Proc Natl Acad Sci USA 93:12382-12387.
Kanagawa T. Bias and artifacts in multitemplate polymerase chain reactions (PCR). J Biosci Bioeng. 2003;96:317-23.
Kasai H, et al.(1993) Formation, inhibition of formation, and repair of oxidative 8-hydroxyguanine DNA damage. Basic Life Sci 61:257-262.
Kaur M, Makrigiorgos GM. Novel amplification of DNA in a hairpin structure: towards a radical elimination of PCR errors from amplified DNA. Nucleic Acids Res. 2003;31:26e1-7.
Kennedy SR, Loeb LA, Herr AJ (2012) Somatic mutations in aging, cancer and neurodegeneration. Mech Ageing Dev 133(4):118-26.

Khaidakov M, Heflich RH, Manjanatha MG, Myers MB, Aidoo A (2003) Accumulation of point mutations in mitochondrial DNA of aging mice. Mutat Res 526:1-7.
Kinde I, Wu J, Papadopoulos N, Kinzler KW, Vogelstein B. Detection and quantification of rare mutations with massively parallel sequencing. Proc Natl Acad Sci USA. 2011;108:9530-5.
Kivioja et al., "Counting absolute numbers of molecules using unique molecular identifiers," Nature Methods 9, dated Jan. 1, 2012, pp. 72-74.
Kozarewa I, Ning Z, Quail MA, Sanders MJ, Berriman M, Turner OJ. Amplification free Illumine sequencing-library preparation facilitates improved mapping and assembly of (G+C)-biased genomes. Nat Methods. 2009; 6:291-5.
Kraytsberg Y, Nicholas A, Caro P, Khrapko K (2008) Single molecule PCR in mtDNA mutational analysis: Genuine mutations vs. damage bypass-derived artifacts. Methods 46:269-273.
Kunkel, TA. Mutational specificity of depurination. Proc Natl Acad Sci USA. 1984; 81:1494-98.
LaTuga MS, Ellis JC, Cotton CM, Goldberg RN, Wynn JL, Jackson RB, et al. Beyond bacteria: a study of the enteric microbial consortium in extremely low birth weight infants. PLoS ONE. 2011; 6:e27858.
Lecroq B, Lejzerowicz F, Bechar D, Christen R, Esling P, Baerlocher L, et al. Ultradeep sequencing of foraminiferal microbarcodes unveils hidden richness of early monothalamous lineages in deep-sea sediments. Proc Natl Acad Sci USA. 2011;108:13177-82.
Lin MT, Simon DK, Ahn CH, Kim LM, Beal MF (2002) High aggregate burden of somatic mtDNA point mutations in aging and Alzheimer's disease brain. Hum Mol Genet 11:133-145.
Lindahl T, Wood RD. Quality control by DNA repair. Science. 1999;286:1897-1905.
Lynch AM, Sasaki jC, Elespuru R, Jacobson-Kram D, Thybaud V, et al. New and emerging technologies for genetic toxicity testing. Environ Mol Mutagen. 2011;52(3):205-23.
Mackelprang R, Waldrop MP, DeAngelis KM, David MM, Chavarria KL, Blazewicz SJ, et al. Metagenomic analysis of a permafrost microbial community reveals a rapid response to thaw. Nature. 2011 ;480:368-71.
McBride T J, Preston BD, Loeb LA (1991) Mutagenic spectrum resulting from DNA damage by oxygen radicals. Biochemistry 30:207-213.
McCloskey ML, Stager R, Hansen RS, Laird CD. Encoding PCR products with batch-stamps and barcodes. Biochem Genet. 2007; 45:761-7.
Metzker ML. Sequencing technologies—the next generation. Nat Rev Genet. 2010;11:31-46.
Meyerhans A, Vartanian JP, Wain-Hobson S. DNA recombination during PCR. Nucleic Acids Research. 1990;18:1687-91.
Miner BE, Stager RJ, Burden AF, Laird CD, Hansen RS. Molecular barcodes detect redundancy and contamination in hairpin-bisulfite PCR. Nucleic Acids Research. 2004;32:e135.
Minot S, Sinha R, Chen J, Li H, Keilbaugh SA, Wu GO, et al. The human gut virome: interindividual variation and dynamic response to diet. Genome Res. 2011; 21:1616-25.
Mitchell PS, Parkin RK, Kroh EM, Fritz BR, Wyman SK, Pogosova-Agadjanyan EL, et al. Circulating microRNAs as stable blood-based markers for cancer detection. Proc Natl Acad Sci USA. 2008; 105:10513-8.
Nasu A, Marusawa H, Ueda Y, Nishijima N, Takahashi K, Osaki Y, et al. Genetic heterogeneity of hepatitis C virus in association with antiviral therapy determined by ultra-deep sequencing. PLoS ONE. 2011;6:e24907.
Out AA, van Minderhout IJHM, Goeman JJ, Ariyurek Y, Ossowski S, Schneeberger K, et al. Deep sequencing to reveal new variants in pooled DNA samples. Hum Mutat. 2009;30:1703-12.
Ozsolak, F., Platt, A.R., Jones, D.R., Reifenberger, J.G., Sass, L.E., Mcinerney, P., Thompson, J.F., Bowers, J., Jarosz, M., and Milos, P.M. (2009). Direct RNA sequencing. Nature 461, 814-818.
Parsons T J, et al. (1997) A high observed substitution rate in the human mitochondrial DNA control region. Nat Genet 15:363-368.
Quail MA, Kozarewa I, Smith F, Scally A, Stephens PJ, Durbin R, et al. A large genome center's improvements to the Illumina sequencing system. Nat Methods. 2008;5:1005-10.

(56) References Cited

OTHER PUBLICATIONS

Roberts et al., "Short template amplicon and multiplex megaprimer-enabled relay (STAMMER) sequencing, a simultaneous approach to higher throughput sequence-based typing of polymorphic genes", Immunogenetics (2010), vol. 62, 253-60.
Salk J, Fox E, Loeb L. Mutational heterogeneity in human cancers: origin and consequences. Annual Review of Pathology. 2009;5:51-75.
Shen Y, Wan Z, Coarfa C, Drabek R, Chen L, Ostrowski EA, et al. A SNP discovery method to assess variant allele probability from next-generation resequencing data. Genome Res. 2010;20:273-80.
Shendure J, Ji H. Next-generation DNA sequencing. Nat Biotechnol. 2008;26:1135-45.
Shibutani S, Takeshita M, Grollman AP. Insertion of specific bases during DNA synthesis past the oxidation-damaged base 8-oxodG. Nature. 1991;349:431-4.
Shiroguchi et al., "Digital RNA sequencing minimizes sequence-dependent bias and amplification noise with optimized single-molecule barcodes", PNAS 109, dated Jan. 9, 2012, pp. 1347-1652.
Song S, et al. (2005) DNA precursor asymmetries in mammalian tissue mitochondria and possible contribution to mutagenesis through reduced replication fidelity. Proc Natl Acad Sci USA 102:4990-4995.
Stiller M, Green RE, Ronan M, Simons JF, Du L, HeW., et al. Patterns of nucleotide misincorporations during enzymatic amplification and direct large-scale sequencing of ancient DNA. Proc Natl Aced Sci USA. 2006; 103:13578-84.
Stoneking M (2000) Hypervariable sites in the mtDNA control region are mutational hotspots. Am J Hum Genet 67:1029-1032.
Thomas DC, Roberts JD, Sabatino RD, Myers TW, et al. Fidelity of mammalian DNA replication and replicative DNA polymerases. Biochemistry. 1991;30:11751-9.
Travers KJ, Chin CS, Rank DR, Eid JS, Turner SW. A flexible and efficient template format for circular consensus sequencing and SNP detection. Nucleic Acids Res. 2010; 38:159e1-8.
USPTO, International Search Report and Written Opinion for PCT/US2013/032665, dated Jul. 9, 2013, 14 pages.
USPTO, Notice of Allowance for U.S. Appl. No. 15/660,785, dated Dec. 27, 2018. 17 pages.
USPTO, Non-Final Office Action for U.S. Appl. No. 16/120,019, dated Nov. 19, 2018. 16 pages.
USPTO, Final Office Action for U.S. Appl. No. 16/120,019, dated Jun. 7, 2019. 17 pages.
USPTO, Notice of Allowance for U.S. Appl. No. 16/120,091, dated Mar. 4, 2019. 9 pages.
USPTO, Notice of Allowance for U.S. Appl. No. 16/120,091, dated Jun. 10, 2019. 8 pages.
USPTO, Non-Final Office Action for U.S. Appl. No. 16/411,045, dated Jul. 25, 2019. 20 pages.
Vandenbroucke I, Van Marek H, Verhasselt P, Thys K, Mostmans W, Dumont S, et al. Minor variant detection in amplicons using 454 massive parallel pyrosequencing: experiences and considerations for successful applications. BioTechniques. 2011;51 :167-77.
Vermulst M, et al. (2007) Mitochondrial point mutations do not limit the natural lifespan of mice. Nat Genet 39:540-543.
Wang C, Mitsuya Y, Gharizadeh B, Ronaghi M, Shafer RW. Characterization of mutation spectra with ultra-deep pyrosequencing: application to HIV-1 drug resistance. Genome Res. 2007;17:1195-201.
Wiemann S, Stegemann J, Grothues D, Bosch A, Estivill X, Schwager C, Zimmermann J, Voss H, Ansorge W. (1995) Simultaneous On-Line DNA Sequencing on Both Strands with Two Fluorescent Dyes. Analytical Biochemistry, vol. 224, pp. 117-121.
Yang J, Yang F, Ren L, Xiong Z, Wu Z, Dong J, et al. Unbiased parallel detection of viral pathogens in clinical samples by use of a metagenomic approach. J Clin Microbial. 2011;49:3463-9.
Zagordi O, Klein R, Daumer M, Beerenwinkel N. Error correction of next-generation sequencing data and reliable estimation of HIV quasispecies. Nucleic Acids Research. 2010;38:7400-9.

Borodina, T. et al. "Chapter five—A Strand-Specific Library Preparation Protocol for RNA Sequencing" Methods in Enzymology, 2011, vol. 500, pp. 79-98.
EPO, Extended European Search Report for Application No. EP20166917.3, dated Sep. 30, 2020. 6 pages.
USPTO, U.S. Appl. No. 16/411,066, Non-Final Office Action, dated Dec. 23, 2019. 33 pgs.
USPTO, U.S. Appl. No. 16/503,382, Non-Final Office Action, dated Jan. 24, 2020. 35 pgs.
USPTO, U.S. Appl. No. 16/503,382, Notice of Allowance with notice of references cited, dated Jul. 15, 2020.
USPTO, U.S. Appl. No. 16/908,611, Non-Final Office Action, dated Oct. 9, 2020. 28 pages.
Withers & Rogers, Opposition against European Patent No. 2828218, dated May 4, 2021, 28 pages.
Margaret Dixon, Opposition against European Patent No. 2828218, dated May 4, 2021, 23 pages.
Lewis Silkin, Opposition against European Patent No. 2828218, dated May 4, 2021, 7 pages.
Kinde et al., Supporting Information corresponding to "Detection and quantification of rare mutations with massively parallel sequencing", PNAS USA 108:9530-9535, Jun. 7, 2011.
Schmitt et al., Supporting Information corresponding to "Detection of ultra-rare mutations by next-generation sequencing", PNAS, Sep. 4, 2012, 109(36) 14508-14513.
Schmitt et al., Corrected Supporting Information corresponding to "Detection of ultra-rare mutations by next-generation sequencing", PNAS, Sep. 4, 2012, 109(36) 14508-14513, Corrected SI dated Mar. 27, 2013.
Shiroguchi et al., Supporting Information corresponding to "Digital RNA sequencing minimizes sequence-dependent bias and amplification noise with optimized single-molecule barcodes", PNAS, ePub 109(4): 1347-1352), Jan. 9, 2012.
USPTO, U.S. Appl. No. 16/503,382, Corrected Notice of Allowance with notice of references cited, dated Jul. 29, 2020.
USPTO, U.S. Appl. No. 16/118,306, Non-Final Office Action, dated Nov. 18, 2020. 50 pages.
USPTO, U.S. Appl. No. 16/118,290, Non-Final Office Action, dated Dec. 14, 2020. 33 pages.
USPTO, U.S. Appl. No. 17/008,395, Non-Final Office Action, dated Jan. 7, 2021, 20 pages.
USPTO, U.S. Appl. No. 16/118,305, Non-Final Office Action, dated Jan. 13, 2021.
USPTO, U.S. Appl. No. 16/908,611, Notice of Allowance, dated Jan. 29, 2021. 11 pages.
USPTO, U.S. Appl. No. 16/119,471, Non-Final Office Action, dated Feb. 2, 2021, 32 pages.
USPTO, U.S. Appl. No. 16/118,286, Non-Final Office Action, dated Mar. 1, 2021.
USPTO, U.S. Appl. No. 16/118,306, Final Office Action, dated Mar. 29, 2021. 17 pages.
USPTO, U.S. Appl. No. 17/008,395, Notice of Allowance, dated Apr. 15, 2021, 13 pages.
USPTO, U.S. Appl. No. 16/118,290, Notice of Allowance, dated Apr. 20, 2021. 5 pages.
Bentley, David R. et al., "Accurate whole human genome sequencing using reversible terminator chemistry," Nature 456:53-59 (2008).
Chiu, R.W.K. et al., "Noninvasive prenatal diagnosis of fetal chromosomal aneuploidy by massively parallel genomic sequencing of DNA in maternal plasma," PNAS 105:20458-20463 (2008).
Diehl, Frank et al., "Basic-Alimentary Tract-Analysis of Mutations in DNA Isolated From Plasma and Stool of Colorectal Cancer Patients", Gastroenterology 135:489-498 (2008).
Diehl, Frank et al., "Detection and quantification of mutations in the plasma of patients with colorectal tumors," PNAS 102:16368-16373 (2005).
Ding, Li et al., "Analysis of next-generation genomic data in cancer: accomplishments and challenges," Human Molecular Genetics, 19:R188-R196 (2010).
Ewing, B. et al. "Base-Calling of Automated Sequencer Traces Using Phred. II. Error Probabilities" Genome Research (1998) vol. 8, pp. 186-194.

(56) References Cited

OTHER PUBLICATIONS

Fleischhacker, M. et al., "Circulating nucleic acids (CNAs) and cancer—A survey," Biochimica et Biophysica Acta. 1775:181-232 (2007).
Fong, Siew Lee et al., "Comparison of 7 Methods for Extracting Cell-Free DNA from Serum Samples of Colorectal Cancer Patients," Clinical Chemistry, 55:587-598 (2009).
Forshew, T. et al. "Noninvasive Identification and Monitoring of Cancer Mutations by Targeted Deep Sequencing of Plasma DNA" Science Translational Medicine (2012) vol. 4, Issue 136, 136ra68, 14 pages.
Gordon, David J. et al., "Causes and consequences of aneuploidy in cancer," Nature Reviews Genetics 13:189-203 (2012).
Jiang, Hui et al., "SeqMap: mapping massive amount of oligonucleotides to the genome," Bioinformatics 24:2395-2396 (2008).
Kao, Wei-Chun et al., "BayesCall: A model-based base-calling algorithm for high-throughput short-read sequencing," Genome Research 19:1884-1895 (2009).
Kircher, Martin et al., "Improved base calling for the Illumina Genome Analyzer using machine learning strategies," Genome Biology 10:R83 (2009).
Kirsch, Stefan et al., "Sequence error storms and the landscape of mutations in cancer," PNAS 109:14289-14290 (2012).
Ledergerber, Christian et al., "Base-calling for next-generation sequencing platforms," Briefings in Bioinformatics 12:489-497 (2011).
Li, Heng et al., "Fast and accurate short read alignment with Burrows-Wheeler transform," Bioinformatics 25:1754-1760 (2009).
Li, Heng et al., "Mapping short DNA sequencing reads and calling variants using mapping quality scores," Genome Research, 18:1851-1858 (2008).
Liang, Kuo-Ching et al., "Bayesian Basecalling for DNA Sequence Analysis Using Hidden Markov Models," IEEE/ACM Transactions on Computational Biology and Bioinformatics, 4:430-440 (2007).
Liao, Gary J.W. et al., "Targeted Massively Parallel Sequencing of Maternal Plasma DNA Permits Efficient and Unbiased Detection of Fetal Alleles," Clinical Chemistry 57:92-101 K2011).
Lo, Y.M. Dennis et al., "Quantitative Analysis of Fetal DNA in Maternal Plasma and Serum: Implications for Noninvasive Prenatal Diagnosis," Am. J. Hum. Genet. 62:768-775 (1998).
Lunter, Gerton et al., "Stampy: A statistical algorithm for sensitive and fast mapping of Illumina sequence reads," Genome Research 21:936-939 (2011).
McKernan, Kevin Judd et al., "Sequence and structural variation in a human genome uncovered by short-read, massively parallel ligation sequencing using two-base encoding," Genome Research 19:1527-1541 (2009).
Mertes, Florian et al., "Targeted enrichment of genomic DNA regions for next-generation sequencing," Briefings in Functional Genomics, 10:374-386 (2011).
Meyer, M. et al. "Targeted high-throughput sequencing of tagged nucleic acid samples" Nucleic Acids Research (2007) vol. 35, No. 15, e97, 5 pages.
Meyerson, Matthew et al., "Advances in understanding cancer genomes through second-generation sequencing," Nature Reviews Genetics, 11:685-696 (2010).
Narayan, A. et al. "Ultrasensitive Measurement of Hotspot Mutations in Tumor DNA in Blood Using Error-Suppressed Multiplexed Deep Sequencing" Cancer Research (2012) vol. 72, No. 14, pp. 3492-3498.
Nielsen, Rasmus et al., "Genotype and SNP calling from next-generation sequencing data," Nature Reviews Genetics, 12:443-451 (2011).
Quinlan, Aaron R. et al., "Pyrobayes: an improved base caller for SNP discovery in pyrosequences," Nature Methods, 5:179-181 (2008).
Redon, Richard et al., "Global variation in copy number in the human genome," Nature 444:444-454 (2006).
Rizzo, J. et al. "Key Principles and Clinical Applications of "Next-Generation" DNA Sequencing" Cancer Prevention Research (2012), vol. 5, No. 7, pp. 887-900.
Schmitt, Michael W. et al., "Detection of ultra-rare mutations by next-generation sequencing," PNAS 109:14508-14513 (2012).
Schwarzenbach, H. et al., "Cell-free nucleic acids as biomarkers in cancer patients," Nature Reviews, 11, 426-437, 2011.
Schweiger, Michal R. et al., "Genome-Wide Massively Parallel Sequencing of Formaldehyde Fixed-Paraffin Embedded (FFPE) Tumor Tissues for Copy-Number- and Mutation-Analysis," PLOS One 4:e5548 (2009).
Sehnert, Amy J. et al., "Optimal Detection of Fetal Chromosomal Abnormalities by Massively Parallel DNA Sequencing of Cell-Free Fetal DNA from Maternal Blood," Clinical Chemistry 57:1042-1049 (2011).
Sparks, Andrew B., et al., "Selective analysis of cell-free DNA in maternal blood for evaluation of fetal trisomy," Prenatal Diagnosis, 32:3-9 (2012).
Teer, Jamie K. et al., "Sequence and structural variation in a human genome uncovered by short-read, massively parallel ligation sequencing using two-base encoding," Genome Research 20:1420-1431 (2010).
USPTO, U.S. Appl. No. 16/120,019, Notice of Allowance, dated Oct. 30, 2019. 15 pgs.
USPTO, U.S. Appl. No. 16/411,045, Notice of Allowance, dated Nov. 15, 2019. 16 pgs.
USPTO, U.S. Appl. No. 16/411,068, Non-Final Office Action, dated Nov. 20, 2019. 28 pgs.
USPTO, U.S. Appl. No. 16/411,069, Non-Final Office Action, dated Nov. 26, 2019. 28 pgs.
Wagle, Nikhil et al., "High-Throughput Detection of Actionable Genomic Alterations in Clinical Tumor Samples by Targeted, Massively Parallel Sequencing," AACR Cancer Discovery 2:82-93 (2011).
USPTO, U.S. Appl. No. 16/119,471, Notice of Allowance, dated May 24, 2021, 11 pages.
USPTO, U.S. Appl. No. 16/118,305, Notice of Allowance, dated Sep. 23, 2021.
USPTO, U.S. Appl. No. 17/361,245, Nonfinal Office Action, dated Nov. 3, 2021.
Craig et al., "Identification of genetic variants using bar-coded multiplexed sequencing," Nature Methods 5 887-93 + supplemental material (Oct. 2008).
Perakis, S. et al., Advances in Circulating Tumor DNA Analysis, Advances in Clinical Chemistry, vol. 80, 2017.
Withers & Rogers, Further Observations filed in Opposition against European Patent No. 2828218, dated Jan. 19, 2022, 8 pages.
Guardant Health, Petition for IPR of U.S. Pat. No. 10,689,699, IPR2022-00449, Paper 3—Petition, Jan. 31, 2022.
Guardant Health, Petition for IPR of U.S. Pat. No. 10,689,699, IPR2022-00449, Ex. 1002—Quackenbush Declaration, Jan. 31, 2022.
Guardant Health, Petition for IPR of U.S. Pat. No. 10,689,699, IPR2022-00450, Paper 3—Petition, Jan. 31, 2022.
Guardant Health, Petition for IPR of U.S. Pat. No. 10,689,699, IPR2022-00450, Ex. 1002—Quackenbush Declaration, Jan. 31, 2022.
USPTO, U.S. Appl. No. 17/392,180, Nonfinal Office Action, mail date Feb. 3, 2022.
USPTO, U.S. Appl. No. 17/392,207, Nonfinal Office Action, mail date: Feb. 18, 2022.
USPTO, U.S. Appl. No. 17/392,185, Nonfinal Office Action, mail date: Feb. 22, 2022.
USPTO, U.S. Appl. No. 17/361,245, Notice of Allowance, mail date: Feb. 25, 2022.
USPTO, U.S. Appl. No. 17/392,203, Nonfinal Office Action, mail date: Mar. 21, 2022.
Guardant Health, Petition for IPR of U.S. Pat. No. 10,760,127, IPR2022-00816, Paper 3—Petition, Apr. 8, 2022.
Guardant Health, Petition for IPR of U.S. Pat. No. 10,760,127, IPR2022-00816, Ex. 1002—Quackenbush Declaration, Apr. 8, 2022.
Guardant Health, Petition for IPR of U.S. Pat. No. 10,760,127, IPR2022-00817, Paper 3—Petition, Apr. 8, 2022.

(56) References Cited

OTHER PUBLICATIONS

Guardant Health, Petition for IPR of U.S. Pat. No. 10,760,127, IPR2022-00817, Ex. 1002—Quackenbush Declaration, Apr. 8, 2022.
Clark, T. et al. "Direct Detection and Sequencing of Damaged DNA Bases" Genome Integrity, 2011, vol. 2, No. 10, 9 pages. (IPR2022-00817 Ex. 1030).
Evans et al., "NEB Expressions" New England BioLabs (2007) (IPR2022-00816 Ex. 1014).
Hodges et al., "Genome-wide in situ exon capture for selective resequencing," Nature Genetics 39(12) (2007) (IPR2022-00817 Ex. 1028).
Illumina, Complete Secondary Analysis Workflow for the Genome Analyzer, Technical Note: Illumina Systems and Software (2009) (IPR2022-00816 Ex. 1011).
Illumina, Preparing Samples for Sequencing Genomic DNA (2007) (IPR2022-00816 Ex. 1008).
McCarthy, "Third Generation DNA Sequencing: Pacific Biosciences' Single Molecule Real Time Technology," Chemistry & Biology 17 (2010) (IPR2022-00817 Ex. 1026).
NEB Expressions, New England BioLabs, https://web.archive.org/web/20080321144426/http://www.neb.com/nebecomm/tech_reference/neb_transcripts.asp (Feb. 23, 2022) (IPR2022-00816 Ex. 1015).
Nisha et al., "Antioxidants and Their Protective Action Against DNA Damage," International Journal of Pharmacology and Pharmaceutical Sciences 3 (2011) (IPR2022-00816 Ex. 1017).
Song et al., "Sensitive and specific single-molecule sequencing of 5-hydroxymethylcytosine," Nature Methods 9(1) (2012) (IPR2022-00816 Ex. 1027).
USPTO, U.S. Appl. No. 17/392,175, Nonfinal Office Action, mail date: Dec. 9, 2021.
USPTO, U.S. Appl. No. 17/392,193, Nonfinal Office Action, mail date: Dec. 13, 2021.
USPTO, U.S. Appl. No. 17/392,175, Final Office Action, mail date: Apr. 13, 2022.
Guardant Health, Inc., Response to Notice of Opposition, European Patent No. 2 893 040 (May 2020).
Guardant Health, Petition for IPR of U.S. Pat. No. 10,752,951, IPR2022-01158, Paper 3—Petition, Jul. 12, 2022.
Guardant Health, Petition for IPR of U.S. Pat. No. 10,752,951, IPR2022-01158, Ex. 1002—Quackenbush Declaration, Jul. 12, 2022.
Guardant Health, Petition for IPR of U.S. Pat. No. 10,752,951, IPR2022-01159, Paper 3—Petition, Jul. 12, 2022.
Guardant Health, Petition for IPR of U.S. Pat. No. 10,752,951, IPR2022-01159, Ex. 1002—Quackenbush Declaration, Jul. 12, 2022.
Guardant Health, Petition for IPR of U.S. Pat. No. 10,689,699, IPR2022-01388, Paper 2—Petition, Aug. 10, 2022.
Guardant Health, Petition for IPR of U.S. Pat. No. 10,689,699, IPR2022-01388, Ex. 1002—Quackenbush Declaration, Aug. 10, 2022.
Guardant Health, Plaintiffs Opening Claim Construction Brief—*TwinStrand Biosciences, Inc., & University of Washington v. Guardant Health, Inc.*, U.S. District Court for the District of Delaware, C.A. No. 21-1126-VAC. Jul. 27, 2022.
Guardant Health, IPR2022-00449, Ex. 1008—EP Application No. 13764186 Prosecution History through Sep. 7, 2020.
Guardant Health, IPR2022-00449, Ex. 1031—U.S. Appl. No. 16/593,633 File History Excerpts, Jan. 31, 2022.
Guardant Health, IPR2022-00449, Ex. 1032—U.S. Appl. No. 16/277,724 Notice of Allowance (dated Jun. 4, 2020).
Guardant Health, IPR2022-00449, Ex. 1033—U.S. Appl. No. 14/712,754 Office Action (dated May 31, 2016).
Guardant Health, IPR2022-00449, Ex. 1038—U.S. Appl. No. 16/672,267 Notice of Allowance (dated Jul. 21, 2021).
Cosmic Data Analyses, Sanger Institute Catalogue of Somatic Mutations in Cancer, obtained from: https://cancer.sanger.ac.uk/cosmic/analyses, Last accessed Jun. 10, 2022.
Krimmel et al., "Ultra-deep sequencing detects ovarian cancer cells in peritoneal fluid and reveals somatic TP53 mutations in noncancerous tissues," PNAS 113(21) (May 24, 2016).

Wang et al., "Briefing in family characteristics of microRNAs and their applications in cancer research," Biochimica et Biophysica Acta 1844 (2014).
USPTO, U.S. Appl. No. 17/392,203, Notice of Allowance, mail date: Jul. 14, 2022, 16 pages.
EPO, Application No. EP2828218, Summons to Attend Oral Proceedings and Preliminary, Non-Binding Opinion, Aug. 3, 2022.
Guardant Health, Invalidity Contentions—*TwinStrand Biosciences, Inc., & University of Washington v. Guardant Health, Inc.*, U.S. District Court for the District of Delaware, C.A. No. 21-1126-VAC. May 17, 2022.
Guardant Health, Petition for IPR of U.S. Pat. No. 10,287,631, IPR2022-00935, Paper 2—Petition, May 6, 2022.
Guardant Health, Petition for IPR of U.S. Pat. No. 10,287,631, IPR2022-00935, Ex. 1002—Quackenbush Declaration, May 6, 2022.
Minoche et al., "Evaluation of genomic high-throughput sequencing data generated on Illumina HiSeq and Genome Analyzer systems," Genome Biology, 12, R112; 1-15. Nov. 8, 2011.
Mattox et al., "Bisulfite-converted duplexes for the strand specific detection and quantification of rare mutations." PNAS, 114; 4733-4738. Apr. 17, 2017.
USPTO, U.S. Appl. No. 17/392,180, Final Office Action, mail date: Jun. 6, 2022. 32 pages.
USPTO, U.S. Appl. No. 17/392,185, Notice of Allowance, mail date: Jun. 10, 2022. 24 pages.
USPTO, U.S. Appl. No. 17/392,207, Notice of Allowance, mail date: Jun. 14, 2022. 12 pages.
USPTO, U.S. Appl. No. 17/392,175, Notice of Allowance, mail date: Oct. 12, 2022, 16 pages.
USPTO, U.S. Appl. No. 17/392,180, Notice of Allowance, mail date: Oct. 13, 2022, 15 pages.
Withers & Rogers (O1), Further Brief Comments filed in Opposition against European Patent No. 2828218, dated Jan. 20, 2023, 11 pages.
Margaret Dixon (O2), Further Comments filed in Opposition against European Patent No. 2828218, dated Jan. 19, 2023, 12 pages.
Lewis Silkin (O3), Further Comments filed in Opposition against European Patent No. 2828218, dated Jan. 20, 2023, 4 pages.
Duncavage et al., "Targeted next generation sequencing of clinically significant gene mutations and translocations in leukemia," Modern Pathology, 25:795-804 (2012).
US District Court, Delaware, Report and Recommendation on Claim Construction by U.S. Magistrate Judge Sherry R. Fallon—*TwinStrand Biosciences, Inc., & University of Washington v. Guardant Health, Inc.*, U.S. District Court for the District of Delaware, C.A. No. 21-1126-VAC, , Dec. 29, 2022.
EPO, Application No. EP20166917.3, Examination Report, dated Mar. 14, 2023, 4 pages.
EPO, Application No. EP13764186.6, Notice of Revocation of Patent No. EP 2828218, dated Mar. 22, 2023, 2 pages.
PTAB, IPR2022-01158, Paper 19, Decision Granting Institution of IPR, Jan. 13, 2023.
PTAB, IPR2022-00817, Paper 14, Decision Granting Institution of IPR, Oct. 13, 2022.
EPO, Application No. EP13764186.6, Decision of Revocation Patent No. EP 2828218 with Written Opinion, dated May 24, 2023, 26 pages.
Guardant Health, IPR2022-00817, Paper 26, Petitioner's Reply re IPR of Patent No. 10,760,127, Apr. 13, 2023.
Guardant Health, IPR2022-00817, Ex. 1033 filed with Petitioner's Reply, Declaration of Dr. Andres Larrea, Apr. 13, 2023.
Guardant Health, IPR2022-00817, Ex. 1037 filed with Petitioner's Reply, Deposition Transcript of Rahul Satija, D. Phil (Mar. 21, 2023).
Guardant Health, IPR2022-00817, Ex. 1039 filed with Petitioner's Reply, Rebuttal Declaration of Dr, John Quackenbush, Apr. 13, 2023.
Guardant Health, IPR2022-01158, Paper 13, Petitioner's Pre-Institution Reply re IPR of Patent No. 10,752,951, Nov. 22, 2022.
Chin, Chen-Shan et al., "The Origin of the Haitian Cholera Outbreak Strain," New England J Medicine, 364 (2011), 33-42, + supplemental information (290 pages) (IPR2022-00817 Ex. 1036).

(56) References Cited

OTHER PUBLICATIONS

Pacific Biosciences Template Preparation and Sequencing Guide, 2010 (IPR2022-00817 Ex. 1035).
Guo et al., "A randomized lentivirus shRNA library construction,"2007. Biochemical and Biophysical Research Communications, vol. 348, pp. 272-276. (Year: 2007).
Hirst etal., "Next generation sequencing based approaches to epigenomics," 2010. Briefings in Functional Genomics, vol. 9, Issue 6, pp. 455-465. (Year:2010).
Myllykangas et al., "Overview of Sequencing Technology Platforms," First Online 2011. Bioinformatics for High Throughput Sequencing, Chapter 2, pp. 11-25. (Year: 2011).
USPTO, U.S. Appl. No. 17/392,203, Nonfinal Office Action, mail date: Oct. 30, 2023, 14 pages.
PTAB, IPR2022-01158, Paper 47, Final Written Decision finding claims 1-28 of U.S. Pat. No. 10,752,951 unpatentable, Jan. 11, 2024.
Guardant Health, IPR2022-00817, Paper 45, Transcript of Oral Hearing held Jun. 15, 2023, Aug. 4, 2023.
Guardant Health, IPR2022-01158, Paper 33, Petitioner's Reply re IPR of U.S. Pat. No. 10,752,951, Jun. 30, 2023.
Guardant Health, IPR2022-01158, Paper 33, Exhibit 1062 filed with Petitioner's Reply, Deep Sequence Data Analysis, Springer-Link, https://link.springer.com/book/10.1007/978-1-62703-514-9, (2013), Jun. 30, 2023.
Guardant Health, IPR2022-01158, Paper 33, Exhibit 1063 filed with Petitioner's Reply, Stoler et al., "Family reunion via error correction: an efficient analysis of duplex sequencing data," BMC Bioinformatics (2020) Jun. 30, 2023.
Guardant Health, IPR2022-01158, Paper 33, Exhibit 1063 filed with Petitioner's Reply, Stoler et al., "Streamlined analysis of duplex sequencing data with Du Novo," Genome Biology (2016), Jun. 30, 2023.
Guardant Health, IPR2022-01158, Paper 33, Exhibit 1066 filed with Petitioner's Reply, Declaration of Dr. Paul T. Spellman (IPR2022-01152) Jun. 30, 2023.
Rusk, N "Uber-accurate sequencing," Nature Methods, 9, 942-943, Jan. 2012.
EPO, Application No. EP20166917.3, Examination Report, Mail Date: Jul. 20, 2023. 4 pages.
EPO, Application No. EP23178659.1, Extended European Search Report, Sep. 22, 2023, 6 pages.
USPTO, U.S. Appl. No. 17/392,175, Notice of Allowance, mail date: Aug. 4, 2023, 14 pages.
USPTO, U.S. Appl. No. 17/392,180, Notice of Allowance, mail date: Aug. 30, 2023, 14 pages.
EPO Boards of Appeal, Communication Forwarding Submission to Parties—Withers & Rogers, Comments in Reponse to Grounds of Appeal, dated Feb. 12, 2024, 153 pages with Annexes I and II.
EPO Boards of Appeal, Communication Forwarding Submission to Parties—Margaret Dixon, Comments in Reponse to Ground pf Appeal, dated Feb. 21, 2024, 50 pages.
EPO Boards of Appeal, Communication Forwarding Submission to Parties—Lewis Silkin, Comments in Response to Grounds of Appeals, dated Feb. 27, 2024, 14 pages.
Caldwell, Randolph B. et al., "Full-length cDNAs from chicken bursal lymphocytes to facilitate gene function analysis,", Genome Biology, Biomed Central Ltd. vol. 6, No. 1, Dec. 23, 2004, page R6.
EPO, Application No. EP20166917.3, Examination Report, Mail Date: Jan. 23, 2024. 7 pages.
TwinStrand's Letter Brief, *TwinStrand Biosciences*, Inc., v. *Guardant Health, Inc.*, No. 1:21-1126 (D. Del.) (Oct. 31, 2023), Exhibit F Accompanying Request for Ex Parte Reexam of U.S. Pat. No. 10,287,631, Jun. 21, 2024.
US District Court, Delaware, Claim Construction Order, TwinStrand *Biosciences, Inc.*, v. *Guardant Health, Inc.*, No. 1:21-1126 (D. Del. (Jun. 12, 2023), Exhibit H Accompanying Request for Ex Parte Reexam of U.S. Pat. No. 10,287,631, Jun. 21, 2024.
Kircher et al., "Addressing Challenges in the Production and Analysis of Illumina Sequencing Data," BMC Genomics 12 (2011), Exhibit J Accompanying Request for Ex Parte Reexam of U.S. Pat. No. 10,287,631, Jun. 21, 2024.
Infringement Report of Lior Pachter (excerpt), *TwinStrand Biosciences, Inc.*, v. *Guardant Health, Inc.*, No. 1:21-1126 (D. Del) (Apr. 7, 2023), Exhibit N Accompanying Request for Ex Parte Reexam of U.S. Pat. No. 10,287,631, Jun. 21, 2024.
Curriculum Vitae of Dr. Peter A Sims, Ex. X Accompanying Request for Exam Parte Reexam of U.S. Pat. No. 10,287,631, Jun. 21, 2024.
Claim Chart CC-LI, Exhibit AA Accompanying Request for Ex Parte Reexam of U.S. Pat. No. 10,287,631, Jun. 21, 2024.
Claim Chart CC-VI, Exhibit BB Accompanying Request for Ex Parte Reexam of U.S. Pat. No. 10,287,631, Jun. 21, 2024.
Declaration of Nathaniel Frank-Wright regarding TruSeq Brochure, Exhibit CC Accompanying Request for Ex Parte Reexam of U.S. Pat. No. 10,287,631, Jun. 21, 2024.
EPO, Application No. EP20166917.3, Examination Report, Mail Date: Jul. 12, 2024. 5 pages.
Guardant Health, Appellant's Opening Brief—*Guardant Health, Inc.* v. *University of Washington*, Appeal No. 24-1129 (appeal of PTAB decision in IPR2022-00817), Apr. 15, 2024.
Guardant Health, Appellant's Reply Brief—*Guardant Health, Inc.* v. *University of Washington*, Appeal No. 24-1129 (appeal of PTAB decision in IPR2022-00817), Aug. 5, 2024.
USPTO, U.S. Appl. No. 17/392,203, Notice of Allowance, Examiner David C. Thomas, mail date: Jun. 4, 2024, 13 pages.
USPTO, Order Granting Request For Ex Parte Reexamination of U.S. Pat. No. 10,287,631; Control No. 90/019,551, Mail Date: Aug. 1, 2024, 19 pages.
Bently, David R. et al., Supplemental Information re "Accurate whole human genome sequencing using reversible terminator chemistry," Nature 456:53-59 (2008).
Illumina, TruSeq RNA and DNA Sample Preparation Kits, Data Sheet: Illumina Sequencing (2010) (IPR2022-00816 Ex. 1012).
EPO, Application No. EP20166917.3, Third Party Observations, Jun. 6, 2024, 3 pages.
Guardant Health, Request for Ex Parte Reexam of U.S. Pat. No. 10,287,631, Jun. 21, 2024, 130 pages.
Declaration of Dr. Peter A. Sims, Ex. G of Request for Ex Parte Reexam of U.S. Pat. No. 10,287,631, Jun. 21, 2024, 205 pages.
Illumina, TruSeq RNA and DNA Sample Preparation Kits, Data Sheet: Illumina Sequencing (2010), Exhibit D of Request for Exam Parte Reexam of U.S. Pat. No. 10,287,631, Jun. 21, 2024, 5 pages.
Guardant Health, Opposition to Petition to Vacate Order Granting Reexam of U.S. Pat. No. 10,287,631, Oct. 15, 2024, 17 pages.
EPO, Application No. EP20166917.3, Examination Report, Mail Date: Jan. 14, 2025, 4 pages.

\* cited by examiner

```
5'    1-TAAC---------------------TCCG-2    3'   (top strand)
3'    2-ATTG---------------------AGGC-1    5'   (bottom strand)
```

B

```
5'    1-TAAC---------------------TCCG-2    3'   (top strand)

5'    1-CGGA---------------------GTTA-2    3'   (bottom strand)
```

C

```
1-TAAC---x------------------------------TCCG-2   (top strand)
2-ATTG---y------------------------------AGGC-1   (bottom strand)
```

Figure 10

Python code for pairing DCS reads among partner strands

```python
import sys
import pysam
from optparse import OptionParser

#This program takes as input a BAM file with DCS SMI's in the header, and searches
for the partner SMI. Reads with paired SMIs are kept. Non-agreeing positions
within a read are replaced with N's.

parser=OptionParser()
parser.add_option("--infile", action="store", type='string', dest="infile",
help="input BAM file", default='sys.stdin')
parser.add_option("--outfile", action="store", type='string', dest="outfile",
help="output BAM file", default='/dev/stdout')
parser.add_option("--readnumloc", action="store", type='int', dest="readnumloc",
help="header field containing read number", default='3')
parser.add_option("--tagloc", action="store", type='int', dest="tagloc",
help="header field containing SMI", default='2')
o, args = parser.parse_args()

inBam = pysam.Samfile( o.infile, "rb" )
readDict = {} dictctr = 0
seqctr = 0
tagmatchctr = 0
partialmatchctr = 0
seqreplacectr = 0
Nctr = 0 first, build a dictionary with read 1 SMI's as key, and the corresponding
sequence as an entry.
for line in inBam :

lineSplit = line.qname
    read = lineSplit.split(":")[o.readnumloc]
    tag = lineSplit.split(":")[o.tagloc]
    if read == '1' and tag not in readDict :

readDict[tag] = [line.seq, '']
        dictctr += 1 if dictctr % 1000000 == 0 :
        print >> sys.stderr, "sequences added to dictionary:", dictctr
        dictctr += 1 inBam.close()
inBam = pysam.Samfile( o.infile, "rb" )

next, evaluate every read 2 SMI for a match in the dictionary for line in inBam :

seqctr += 1
    lineSplit = line.qname
    read = lineSplit.split(":")[o.readnumloc]
```

Figure 10 (cont.)

```
        tag = lineSplit.split(":")[o.tagloc]
        switchtag = tag[10:20] + tag[:10]

if read == '2' and switchtag in readDict :
            tagmatchctr += 1 if len(line.seq) == len(readDict[switchtag][0]) :
                newSeq = ''
                for i in xrange (len(line.seq) ) :

if line.seq[i] == readDict[switchtag][0][i] :
                        newSeq = newSeq + line.seq[i]
                    else :
                        newSeq = newSeq + 'N' if line.seq != readDict[switchtag][0] and newSeq.count('N') < 20 :
                    partialmatchctr += 1
                    Nctr += newSeq.count('N')

if newSeq.count('N') < (readDict[switchtag][1]).count('N') or (
readDict[switchtag][1] == '' and newSeq.count('N') < 20 ) :
                    readDict[switchtag][1] = newSeq
                    seqreplacectr += 1 if seqctr % 1000000 == 0 :
        print >> sys.stderr, "tags processed for matches:", seqctr
        print >> sys.stderr, "tag matches:", tagmatchctr
        print >> sys.stderr, "total sequence matches:", seqreplacectr
        print >> sys.stderr, "reads containing disagreeing bases (replaced with
N's):", partialmatchctr
        print >> sys.stderr, "number of N's added:", Nctr inBam.close()

Done generating tag dictionary. Reinterate over bamfile and write entries that
have a sequence match.

inBam = pysam.Samfile( o.infile, "rb" )
outBam = pysam.Samfile ( o.outfile, "wb", template=inBam)

printlinectr = 0
printlinematch = 0 for line in inBam :

printlinectr += 1 lineSplit = line.qname tag = lineSplit.split(":")[o.tagloc]
    read = lineSplit.split(":")[o.readnumloc]

if tag in readDict and read == '1' and len (readDict[tag][1]) > 0 :

line.seq = readDict[tag][1]
        readDict[tag][1] = ''
```

Figure 10 (cont.)

```
            printlinematch += 1
            outBam.write(line)

if printlinectr % 1000000 == 0:
        print >> sys.stderr, "Lines evaluated for printing:", printlinectr
        print >> sys.stderr, "Matching sequences printed:", printlinematch print >> sys.stderr, "Total tags processed for matches:", seqctr
print >> sys.stderr, "Total tag matches:", tagmatchctr
print >> sys.stderr, "Total sequence matches:", seqreplacectr
print >> sys.stderr, "Total reads containing disagreeing bases (replaced with
N's):", partialmatchctr
print >> sys.stderr, "total number of N's added:", Nctr inBam.close()
outBam.close()
```

METHODS OF LOWERING THE ERROR RATE OF MASSIVELY PARALLEL DNA SEQUENCING USING DUPLEX CONSENSUS SEQUENCING

PRIORITY CLAIM

This application is a continuation of U.S. patent application Ser. No. 16/120,072, filed Aug. 31, 2018 and now, which is a continuation of Ser. No. 15/660,785, filed Jul. 26, 2017 and now U.S. Pat. No. 10,287,631, which is a continuation of U.S. patent application Ser. No. 14/386,800, filed Sep. 20, 2014 and now U.S. Pat. No. 9,752,188, which is a U.S. national stage application of International Application No. PCT/US2013/032665, filed Mar. 15, 2013, which claims priority to U.S. Provisional Patent Application No. 61/613,413, filed Mar. 20, 2012; U.S. Provisional Patent Application No. 61/625,623, filed Apr. 17, 2012; and U.S. Provisional Patent Application No. 61/625,319, filed Apr. 17, 2012; the subject matter of all of which are hereby incorporated by reference as if fully set forth herein.

STATEMENT OF GOVERNMENT INTEREST

This invention was made with government support under Grant Nos. F30AG033485, R01CA102029 and R01CA115802 awarded by the National Institutes of Health. The government has certain rights in the invention.

BACKGROUND

The advent of massively parallel DNA sequencing has ushered in a new era of genomic exploration by making simultaneous genotyping of hundreds of billions of basepairs possible at small fraction of the time and cost of traditional Sanger methods [1]. Because these technologies digitally tabulate the sequence of many individual DNA fragments, unlike conventional techniques which simply report the average genotype of an aggregate collection of molecules, they offer the unique ability to detect minor variants within heterogeneous mixtures [2].

This concept of "deep sequencing" has been implemented in a variety fields including metagenomics [3,4], paleogenomics [5], forensics [6], and human genetics [7, 8] to disentangle subpopulations in complex biological samples. Clinical applications, such prenatal screening for fetal aneuploidy [9, 10], early detection of cancer [11] and monitoring its response to therapy [12, 13] with nucleic acid-based serum biomarkers, are rapidly being developed. Exceptional diversity within microbial [14, 15] viral [16-18] and tumor cell populations [19, 20] has been characterized through next-generation sequencing, and many low-frequency, drug-resistant variants of therapeutic importance have been so identified [12, 21, 22]. Previously unappreciated intra-organismal mosasism in both the nuclear [23] and mitochondrial [24, 25] genome has been revealed by these technologies, and such somatic heterogeneity, along with that arising within the adaptive immune system [13], may be an important factor in phenotypic variability of disease.

Deep sequencing, however, has limitations. Although, in theory, DNA subpopulations of any size should be detectable when deep sequencing a sufficient number of molecules, a practical limit of detection is imposed by errors introduced during sample preparation and sequencing. PCR amplification of heterogeneous mixtures can result in population skewing due to stoichastic and non-stoichastic amplification biases and lead to over- or under-representation of particular variants [26]. Polymerase mistakes during pre-amplification generate point mutations resulting from base mis-incorporations and rearrangements due to template switching [26, 27]. Combined with the additional errors that arise during cluster amplification, cycle sequencing and image analysis, approximately 1% of bases are incorrectly identified, depending on the specific platform and sequence context [2, 28]. This background level of artifactual heterogeneity establishes a limit below which the presence of true rare variants is obscured [29].

A variety of improvements at the level of biochemistry [30-32] and data processing [19, 21, 28, 32, 33] have been developed to improve sequencing accuracy. The ability to resolve subpopulations below 0.1%, however, has remained elusive. Although several groups have attempted to increase sensitivity of sequencing, several limitations remain. For example techniques whereby DNA fragments to be sequenced are each uniquely tagged [34, 35] prior to amplification [36-41] have been reported. Because all amplicons derived from a particular starting molecule will bear its specific tag, any variation in the sequence or copy number of identically tagged sequencing reads can be discounted as technical error. This approach has been used to improve counting accuracy of DNA [38, 39, 41] and RNA templates [37, 38, 40] and to correct base errors arising during PCR or sequencing [36, 37, 39]. Kinde et. al. reported a reduction in error frequency of approximately 20-fold with a tagging method that is based on labeling single-stranded DNA fragments with a primer containing a 14 bp degenerate sequence. This allowed for an observed mutation frequency of ~0.001% mutations/bp in normal human genomic DNA [36]. Nevertheless, a number of highly sensitive genetic assays have indicated that the true mutation frequency in normal cells is likely to be far lower, with estimates of per-nucleotide mutation frequencies generally ranging from $10^{-9}$ to $10^{-11}$ [42]. Thus, the mutations seen in normal human genomic DNA by Kinde et al. are likely the result of significant technical artifacts.

Traditionally, next-generation sequencing platforms rely upon generation of sequence data from a single strand of DNA. As a consequence, artifactual mutations introduced during the initial rounds of PCR amplification are undetectable as errors—even with tagging techniques—if the base change is propagated to all subsequent PCR duplicates. Several types of DNA damage are highly mutagenic and may lead to this scenario. Spontaneous DNA damage arising from normal metabolic processes results in thousands of damaging events per cell per day [43]. In addition to damage from oxidative cellular processes, further DNA damage is generated ex vivo during tissue processing and DNA extraction [44]. These damage events can result in frequent copying errors by DNA polymerases: for example a common DNA lesion arising from oxidative damage, 8-oxoguanine, has the propensity to incorrectly pair with adenine during complementary strand extension with an overall efficiency greater than that of correct pairing with cytosine, and thus can contribute a large frequency of artifactual G→T mutations [45]. Likewise, deamination of cytosine to form uracil is a particularly common event which leads to the inappropriate insertion of adenine during PCR, thus producing artifactual C→T mutations with a frequency approaching 100% [46].

It would be desirable to develop an approach for tag-based error correction, which reduces or eliminates artifactual mutations arising from DNA damage, PCR errors, and sequencing errors; allows rare variants in heterogeneous populations to be detected with unprecedented sensitivity;

and which capitalizes on the redundant information stored in complexed double-stranded DNA.

SUMMARY

In one embodiment, a single molecule identifier (SMI) adaptor molecule for use in sequencing a double-stranded target nucleic acid molecule is provided. Said SMI adaptor molecule includes a single molecule identifier (SMI) sequence which comprises a degenerate or semi-degenerate DNA sequence; and an SMI ligation adaptor that allows the SMI adaptor molecule to be ligated to the double-stranded target nucleic acid sequence. The SMI sequence may be single-stranded or double-stranded. In some embodiments, the double-stranded target nucleic acid molecule is a double-stranded DNA or RNA molecule.

In another embodiment, a method of obtaining the sequence of a double-stranded target nucleic acid is provided (also known as Duplex Consensus Sequencing or DCS) is provided. Such a method may include steps of ligating a double-stranded target nucleic acid molecule to at least one SMI adaptor molecule to form a double-stranded SMI-target nucleic acid complex; amplifying the double-stranded SMI-target nucleic acid complex, resulting in a set of amplified SMI-target nucleic acid products; and sequencing the amplified SMI-target nucleic acid products.

In some embodiments, the method may additionally include generating an error-corrected double-stranded consensus sequence by (i) grouping the sequenced SMI-target nucleic acid products into families of paired target nucleic acid strands based on a common set of SMI sequences; and (ii) removing paired target nucleic acid strands having one or more nucleotide positions where the paired target nucleic acid strands are non-complementary (or alternatively removing individual nucleotide positions in cases where the sequence at the nucleotide position under consideration disagrees among the two strands). In further embodiments, the method confirms the presence of a true mutation by (i) identifying a mutation present in the paired target nucleic acid strands having one or more nucleotide positions that disagree; (ii) comparing the mutation present in the paired target nucleic acid strands to the error corrected double-stranded consensus sequence; and (iii) confirming the presence of a true mutation when the mutation is present on both of the target nucleic acid strands and appears in all members of a paired target nucleic acid family.

BRIEF DESCRIPTION OF THE DRAWINGS

FIG. 4 illustrates an example of how a SMI sequence with n-mers of 4 nucleotides in length (4-mers) are read by Duplex Consensus Sequencing (DCS) according to some embodiments. (A) shows the 4-mers with the PCR primer binding sites (or flow cell sequences) 1 and 2 indicated at each end. (B) shows the same molecules as in (A) but with the strands separated and the lower strand now written in the 5'-3' direction. When these molecules are amplified with PCR and sequenced, they will yield the following sequence reads: The top strand will give a read 1 file of TAAC--- and a read 2 file of GCCA---. Combining the read 1 and read 2 tags will give TAACCGGA as the SMI for the top strand. The bottom strand will give a read 1 file of CGGA---- and a read 2 file of TAAC---. Combining the read 1 and read 2 tags will give CGGATAAC as the SMI for the bottom strand. (C) illustrates the orientation of paired strand mutations in DCS. In the initial DNA duplex shown in FIGS. 4A and 4B, a mutation "x" (which is paired to a complementary nucleotide "y") is shown on the left side of the DNA duplex. The "x" will appear in read 1, and the complementary mutation on the opposite strand, "y," will appear in read 2. Specifically, this would appear as "x" in both read 1 and read 2 data, because "y" in read 2 is read out as "x" by the sequencer owing to the nature of the sequencing primers, which generate the complementary sequence during read 2.

is plotted for every position in the ~16-kb mitochondrial genome. Due to the substantial background of technical error, no obvious mutational pattern is discernible by this method. (C) DCS analysis eliminates sequencing artifacts and reveals the true distribution of mitochondrial mutations to include a striking excess adjacent to the mtDNA origin of replication. (D) SSCS analysis yields a large excess of G→T mutations relative to complementary C→A mutations, consistent with artifacts from damaged-induced 8-oxo-G lesions during PCR. All significant (P<0.05) differences between paired reciprocal mutation frequencies are noted. (E) DCS analysis removes the SSCS strand bias and reveals the true mtDNA mutational spectrum to be characterized by an excess of transitions.

Figure 6:
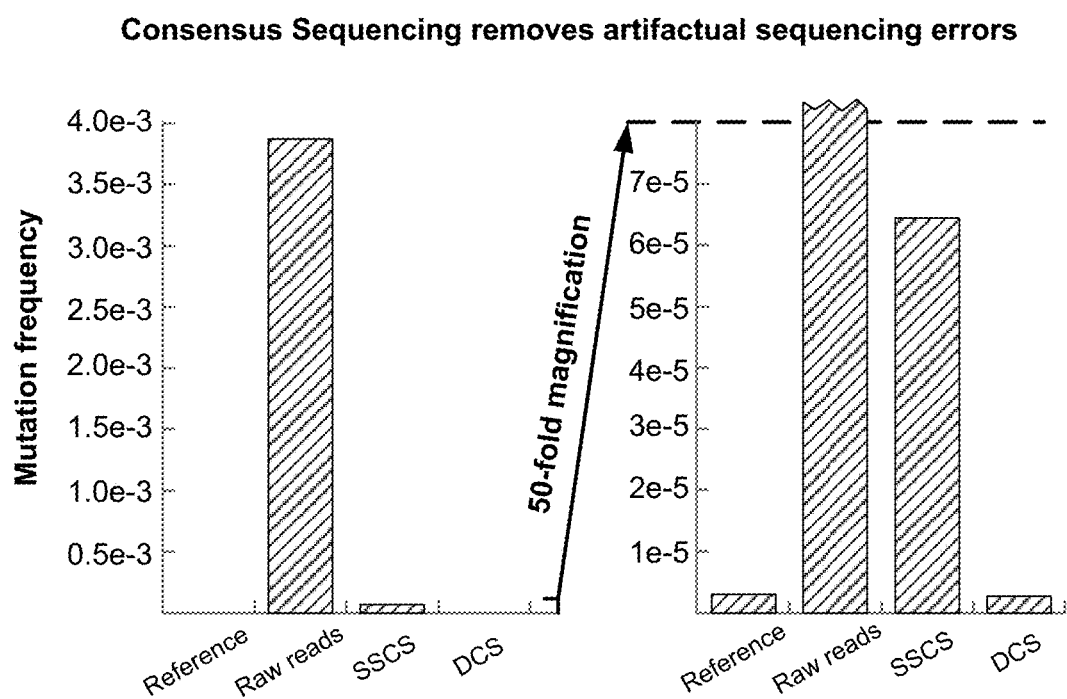

FIG. 6 shows that consensus sequencing removes artifactual sequencing errors as compared to Raw Reads. Duplex Consensus Sequencing (DCS) results in an approximately equal number of mutations as the reference and single strand consensus sequencing (SSCS).

Figure 7:
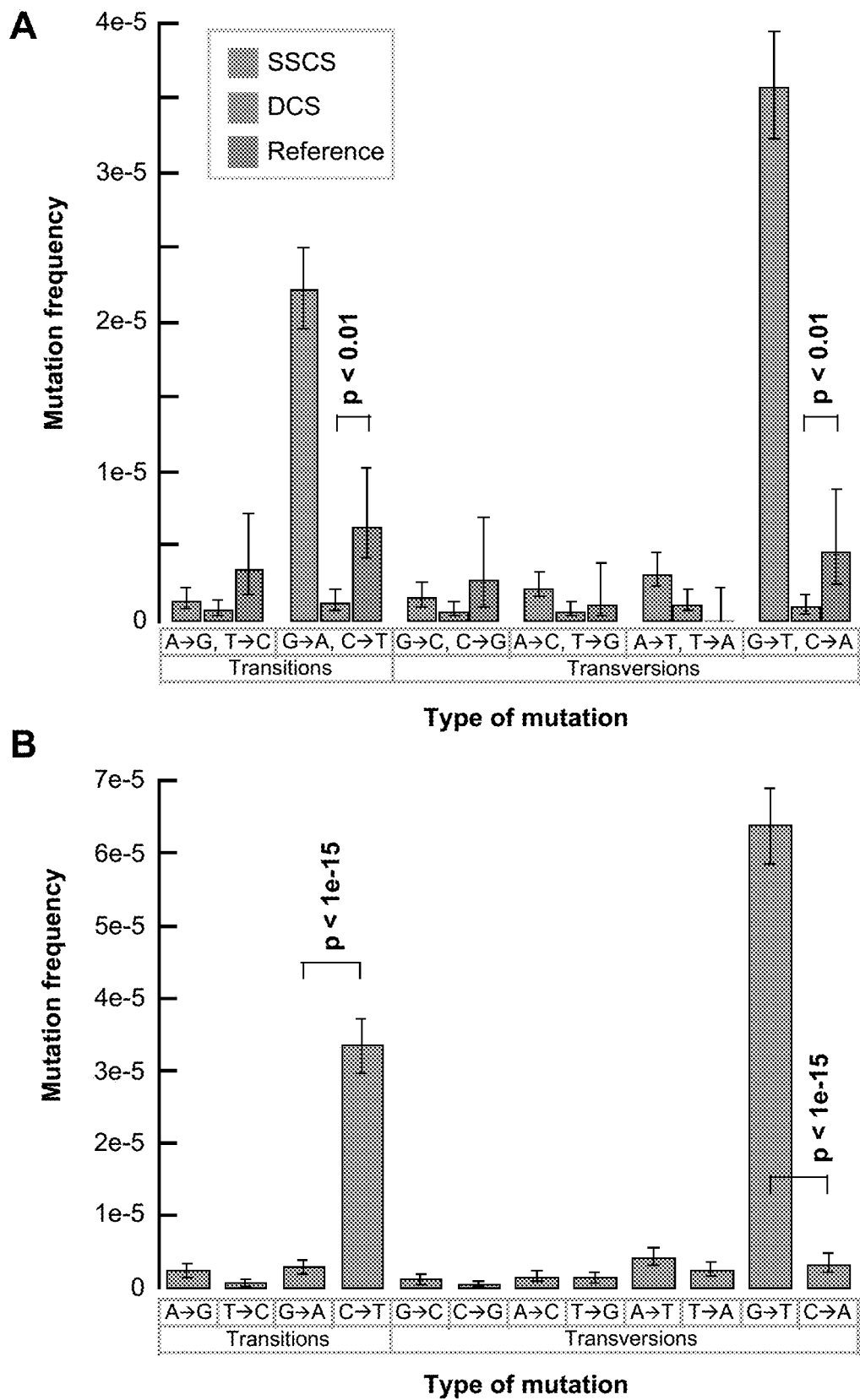

FIG. 7 illustrates duplex sequencing of M13mp2 DNA. (A) Single-strand consensus sequences (SSCSs) reveal a large excess of G→A/C→T and G→T/C→A mutations, whereas duplex consensus sequences (DCSs) yield a balanced spectrum. Mutation frequencies are grouped into reciprocal mispairs, as DCS analysis only scores mutations present in both strands of duplex DNA. All significant (P<0.05) differences between DCS analysis and the literature reference values are noted. (B) Complementary types of mutations should occur at approximately equal frequencies within a DNA fragment population derived from duplex molecules. However, SSCS analysis yields a 15-fold excess of G→T mutations relative to C→A mutations and an 11-fold excess of C→T mutations relative to G→A mutations. All significant (P<0.05) differences between paired reciprocal mutation frequencies are noted.

Figure 8:
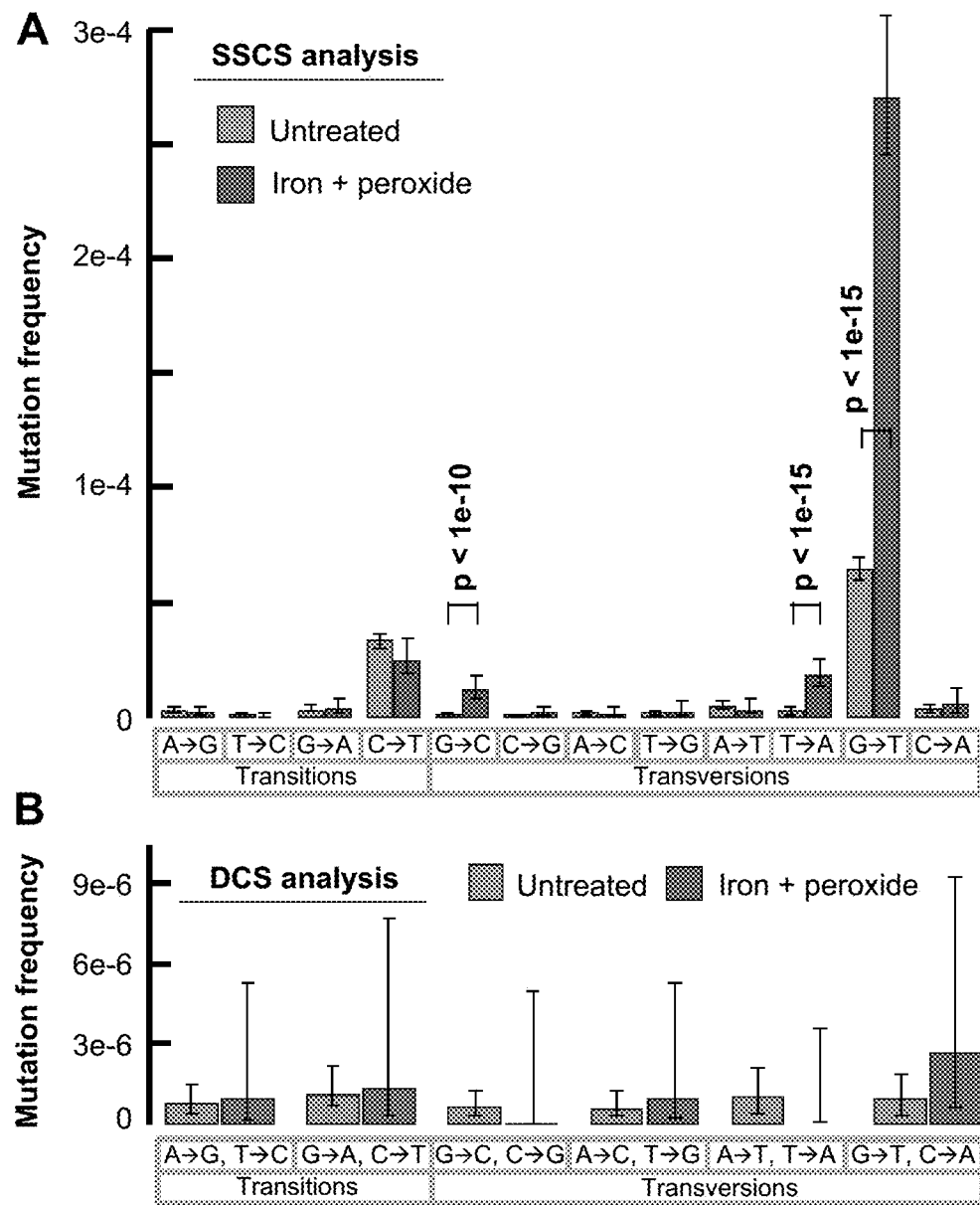

FIG. 8 shows the effect of DNA damage on the mutation spectrum. DNA damage was induced by incubating purified M13mp2 DNA with hydrogen peroxide and FeSO4. (A) SSCS analysis reveals a further elevation from baseline of G→T mutations, indicating these events to be the artifactual consequence of nucleotide oxidation. All significant (P<0.05) changes from baseline mutation frequencies are noted. (B) Induced DNA damage had no effect on the overall frequency or spectrum of DCS mutations.

Figure 9:
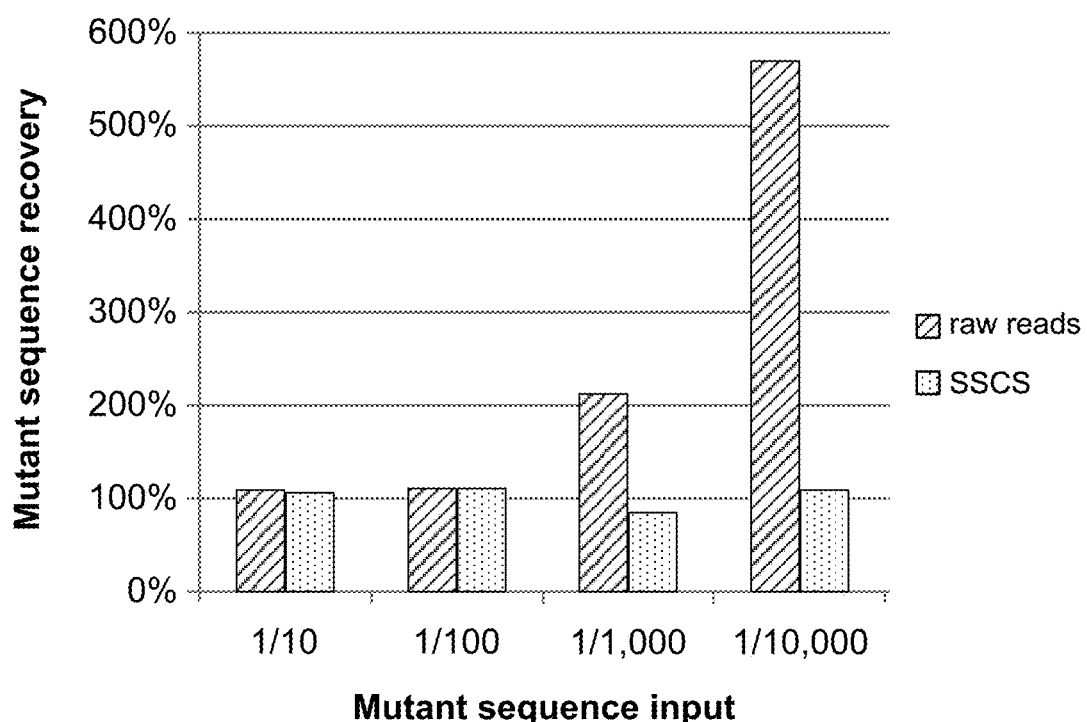

FIG. 9 shows duplex sequencing results in accurate recovery of spiked-control mutations. A series of variants of M13mp2 DNA, each harboring a known single-nucleotide substitution, were mixed in together at known ratios and the mixture was sequenced to 20,000-fold final depth. Standard sequencing analysis cannot accurately distinguish mutants present at a ratio of less than 1/100, because artifactual mutations occurring at every position obscure the presence of less abundant true mutations, rendering apparent recovery greater than 100%. Duplex consensus sequences, in contrast, accurately identify spiked-in mutations down to the lowest tested ratio of 1/10,000.

FIG. 10 is a Python Code that may used to carry out methods described herein according to one embodiment.

DETAILED DESCRIPTION

Figure 2:
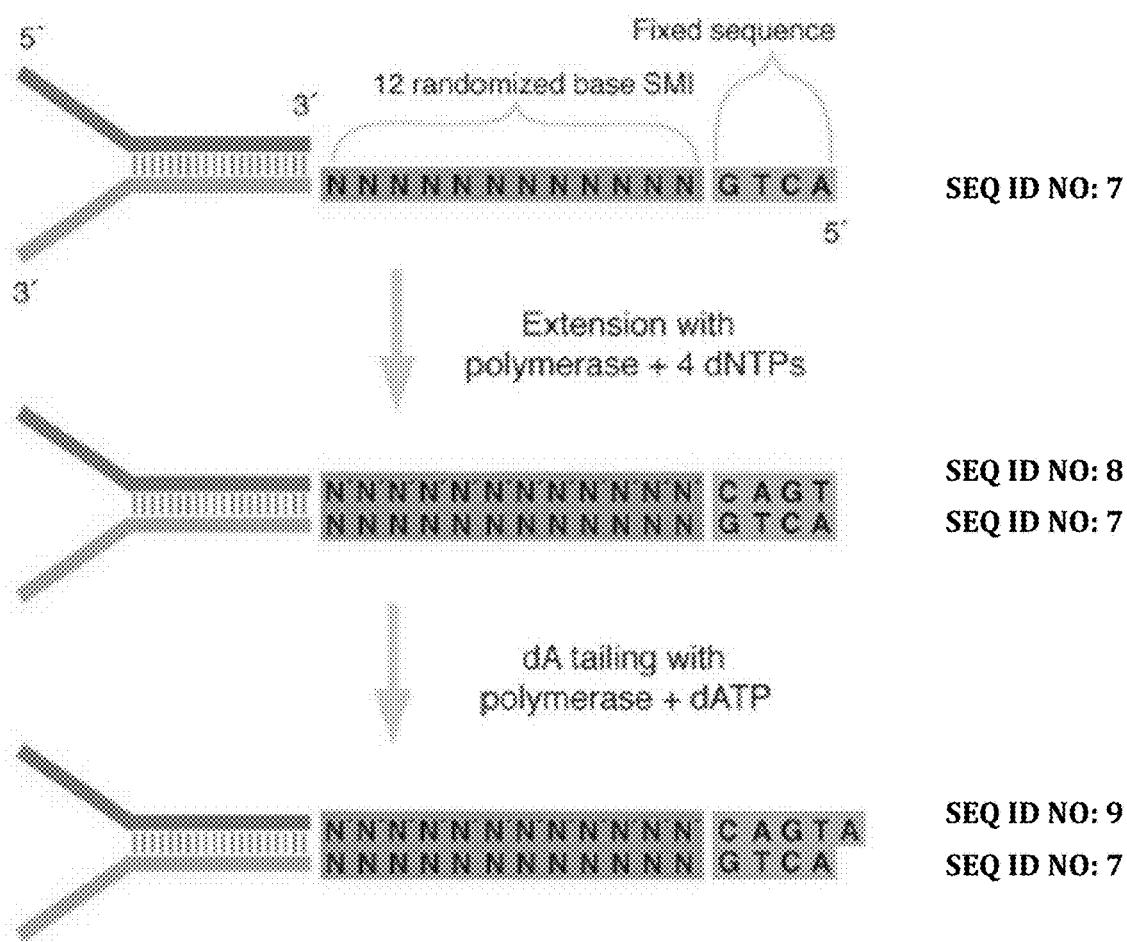
FIG. 2 illustrates Single Molecule Identifier (SMI) adaptor synthesis according to one embodiment. Oligonucleotides are annealed and the complement of the degenerate lower arm sequence (N's) plus adjacent fixed bases is produced by polymerase extension of the upper strand in the presence of all four dNTPs. After reaction cleanup, complete adaptor A-tailing is ensured by extended incubation with polymerase and dATP.

Single molecule identifier adaptors and methods for their use are provided herein. According to the embodiments described herein, a single molecule identifier (SMI) adaptor molecule is provided. Said SMI adaptor molecule is double stranded, and may include a single molecule identifier (SMI) sequence, and an SMI ligation adaptor (FIG. 2). Optionally, the SMI adaptor molecule further includes at least two PCR primer binding sites, at least two sequencing primer binding sites, or both.

The SMI adaptor molecule may form a "Y-shape" or a "hairpin shape." In some embodiments, the SMI adaptor molecule is a "Y-shaped" adaptor, which allows both strands to be independently amplified by a PCR method prior to sequencing because both the top and bottom strands have binding sites for PCR primers FC1 and FC2 as shown in the examples below. A schematic of a Y-shaped SMI adaptor molecule is also shown in FIG. 2. A Y-shaped SMI adaptor requires successful amplification and recovery of both strands of the SMI adaptor molecule. In one embodiment, a modification that would simplify consistent recovery of both strands entails ligation of a Y-shaped SMI adaptor molecule to one end of a DNA duplex molecule, and ligation of a "U-shaped" linker to the other end of the molecule. PCR amplification of the hairpin-shaped product will then yield a linear fragment with flow cell sequences on either end. Distinct PCR primer binding sites (or flow cell sequences FC1 and FC2) will flank the DNA sequence corresponding to each of the two SMI adaptor molecule strands, and a given sequence seen in Read 1 will then have the sequence corresponding to the complementary DNA duplex strand seen in Read 2. Mutations are scored only if they are seen on both ends of the molecule (corresponding to each strand of the original double-stranded fragment), i.e. at the same position in both Read 1 and Read 2. This design may be accomplished as described in the examples relating to double stranded SMI sequence tags.

In other embodiments, the SMI adaptor molecule is a "hairpin" shaped (or "U-shaped") adaptor. A hairpin DNA product can be used for error correction, as this product contains both of the two DNA strands. Such an approach allows for reduction of a given sequencing error rate N to a lower rate of $N*N*(\frac{1}{3})$, as independent sequencing errors would need to occur on both strands, and the same error among all three possible base substitutions would need to occur on both strands. For example, the error rate of $\frac{1}{100}$ in the case of Illumina sequencing [32] would be reduced to $(\frac{1}{100})*(\frac{1}{100})*(\frac{1}{3})=\frac{1}{30,000}$.

An additional, more remarkable reduction in errors can be obtained by inclusion of a single-stranded SMI in either the hairpin adaptor or the "Y-shaped" adaptor will also function to label both of the two DNA strands. Amplification of hairpin-shaped DNA may be difficult as the polymerase must synthesize through a product containing significant regions of self-complementarity, however, amplification of hairpin-shaped structures has already been established in the technique of hairpin PCR, as described below. Amplification using hairpin PCR is further described in detail in U.S. Pat. No. 7,452,699, the subject matter of which is hereby incorporated by reference as if fully set forth herein.

According to the embodiments described herein, the SMI sequence (or "tag") may be a double-stranded, complementary SMI sequence or a single-stranded SMI sequence. In some embodiments, the SMI adaptor molecule includes an SMI sequence (or "tag") of nucleotides that is degenerate or semi-degenerate. In some embodiments, the degenerate or semi-degenerate SMI sequence may be a random degenerate sequence. A double-stranded SMI sequence includes a first degenerate or semi-degenerate nucleotide n-mer sequence and a second n-mer sequence that is complementary to the first degenerate or semi-degenerate nucleotide n-mer sequence, while a single-stranded SMI sequence includes a first degenerate or semi-degenerate nucleotide n-mer sequence. The first and/or second degenerate or semi-degenerate nucleotide n-mer sequences may be any suitable length to produce a sufficiently large number of unique tags to label a set of sheared DNA fragments from a segment of DNA. Each n-mer sequence may be between approximately 3 to 20 nucleotides in length. Therefore, each n-mer sequence may be approximately 4, 5, 6, 7, 8, 9, 10, 11, 12, 13, 14, 15, 16, 17, 18, 19, 20 nucleotides in length. In one embodiment, the SMI sequence is a random degenerate nucleotide n-mer sequence which is 12 nucleotides in length. A 12 nucleotide SMI n-mer sequence that is ligated to each end of a target nucleic acid molecule, as described in the Example below, results in generation of up to $4^{24}$ (i.e., $2.8 \times 10^{14}$) distinct tag sequences.

In some embodiments, the SMI tag nucleotide sequence may be completely random and degenerate, wherein each sequence position may be any nucleotide. (i.e., each position, represented by "X," is not limited, and may be an adenine (A), cytosine (C), guanine (G), thymine (T), or uracil (U)) or any other natural or non-natural DNA or RNA nucleotide or nucleotide-like substance or analog with base-pairing properties (e.g., xanthosine, inosine, hypoxanthine, xanthine, 7-methylguanine, 7-methylguanosine, 5,6-dihydrouracil, 5-methylcytosine, dihydouridine, isocytosine, isoguanine, deoxynucleosides, nucleosides, peptide nucleic acids, locked nucleic acids, glycol nucleic acids and threose nucleic acids). The term "nucleotide" as described herein, refers to any and all nucleotide or any suitable natural or non-natural DNA or RNA nucleotide or nucleotide-like substance or analog with base pairing properties as described above. In other embodiments, the sequences need not contain all possible bases at each position. The degenerate or semi-degenerate n-mer sequences may be generated by a polymerase-mediated method described in the Example below, or may be generated by preparing and annealing a library of individual oligonucleotides of known sequence. Alternatively, any degenerate or semi-degenerate n-mer sequences may be a randomly or non-randomly fragmented double stranded DNA molecule from any alternative source that differs from the target DNA source. In some embodiments, the alternative source is a genome or plasmid derived from bacteria, an organism other than that of the target DNA, or a combination of such alternative organisms or sources. The random or non-random fragmented DNA may be introduced into SMI adaptors to serve as variable tags. This may be accomplished through enzymatic ligation or any other method known in the art.

In some embodiments, the SMI adaptor molecules are ligated to both ends of a target nucleic acid molecule, and then this complex is used according to the methods described below. In certain embodiments, it is not necessary to include n-mers on both adapter ends, however, it is more convenient because it means that one does not have to use two different types of adaptors and then select for ligated fragments that have one of each type rather than two of one type. The ability to determine which strand is which is still possible in the situation wherein only one of the two adaptors has a double-stranded SMI sequence.

In some embodiments, the SMI adaptor molecule may optionally include a double-stranded fixed reference sequence downstream of the n-mer sequences to help make ligation more uniform and help computationally filter out errors due to ligation problems with improperly synthesized adaptors. Each strand of the double-stranded fixed reference sequence may be 4 or 5 nucleotides in length sequence, however, the fixed reference sequence may be any suitable length including, but not limited to 3, 4, 5 or 6 nucleotides in length.

The SMI ligation adaptor may be any suitable ligation adaptor that is complementary to a ligation adaptor added to a double-stranded target nucleic acid sequence including, but not limited to a T-overhang, an A-overhang, a CG overhang, a blunt end, or any other ligatable sequence. In some embodiments, the SMI ligation adaptor may be made using a method for A-tailing or T-tailing with polymerase extension; creating an overhang with a different enzyme; using a restriction enzyme to create a single or multiple nucleotide overhang, or any other method known in the art.

According to the embodiments described herein, the SMI adaptor molecule may include at least two PCR primer or "flow cell" binding sites: a forward PCR primer binding site (or a "flow cell 1" (FC1) binding site); and a reverse PCR primer binding site (or a "flow cell 2" (FC2) binding site). The SMI adaptor molecule may also include at least two sequencing primer binding sites, each corresponding to a sequencing read. Alternatively, the sequencing primer binding sites may be added in a separate step by inclusion of the necessary sequences as tails to the PCR primers, or by ligation of the needed sequences. Therefore, if a double-stranded target nucleic acid molecule has an SMI adaptor molecule ligated to each end, each sequenced strand will have two reads—a forward and a reverse read.

Double-Stranded SMI Sequences

Adaptor 1 (shown below) is a Y-shaped SMI adaptor as described above (the SMI sequence is shown as X's in the top strand (a 4-mer), with the complementary bottom strand sequence shown as Y's):

(Adaptor 1)

Adaptor 2 (shown below) is a hairpin (or "U-shaped") linker:

(Adaptor 2)

Following ligation of both adaptors to a double-stranded target nucleic acid, the following is structure is obtained:

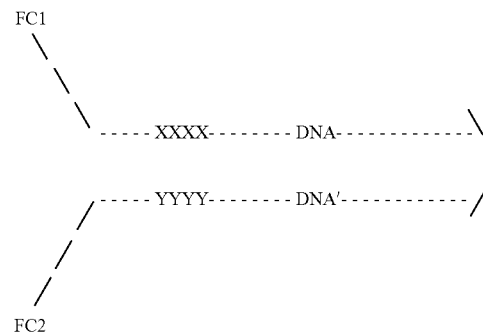

When melted, the product will be of the following form (where "linker" is the sequence of adaptor 2):

FC1-------XXXX------DNA---------linker---------
DNA'----------YYYY--------FC2

This product is then PCR amplified. The reads will yield:

Read 1:

XXXX-----DNA----

Read 2 (note that read 2 is seen as the complement of the bases sequenced:)

XXXX-----DNA----

The sequences of the two duplex strands seen in the two sequence reads may then be compared, and sequence information and mutations will be scored only if the sequence at a given position matches in both of the reads.

This approach does not strictly require the use of an SMI tag, as the sheared ends can be used as identifiers to differentiate unique individual molecules from PCR duplicates. Thus the same concept would apply if one used any standard sequencing adaptor as "Adaptor 1" and the U---shaped linker as "Adaptor 2." However described below, there are a limited number of shear points flanking any given genomic position and thus the power to sequence deeply is increased via inclusion of the SMI tag. A hybrid method using a combination of sheared ends and a shorter n-mer tag (such as 1 or 2 or 3 or 4 or more degenerate or semi-degenerate bases) in the adaptor may also serve as unique molecular identifiers. Another design may include use of any sequencing adaptor (such as one lacking an n-mer tag) in conjunction with an n-mer tag that is incorporated into the U-shaped linker molecule. Such a design would be of the following form (where X and Y represent complementary degenerate or semi-degenerate nucleotides):

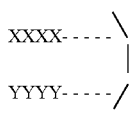

Synthesis of such a design may be obtained in a number of ways, for example synthesizing a set of hairpin oligonucleotides in which each individual oligonucleotide encodes a complementary n-mer sequence, or alternatively by using a DNA polymerase to carry out extension from the following product (where X's represent degenerate nucleotides):

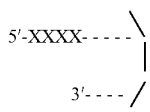

Inclusion of the SMI tag is also extremely useful for identifying correct ligation products, as the assay uses two distinct adaptors. This will yield multiple possible ligation products:

Product I. Adaptor 1---------DNA---------Adaptor 2, which yields the desired product:

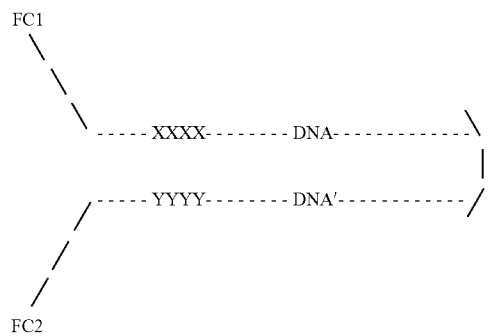

Product II. Adaptor 1---------DNA---------Adaptor 1. This will result in the DNA being amplified as two separate strands, i.e. as occurs in the DCS approach described elsewhere in this document (the second copy of Adaptor 1 is shown below with the SMI as AAA-BBB to emphasize that every DCS adaptor has a distinct SMI sequence)

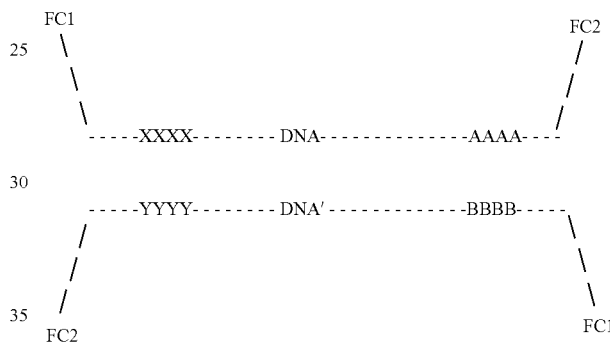

Product III. Adaptor 2---------DNA---------Adaptor 2. This will result in a non-amplifiable circular product shown below:

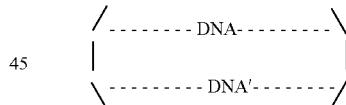

Product III is non-amplifiable, given the absence of primer binding sites and thus will not be present in the final DNA sequences. Thus only Product II needs to be avoided. The formation of Product II can be minimized in the ligation step by using an excess of Adaptor 2 (relative to Adaptor 1). Then primarily Products I and III will be obtained, with minimal formation of Product II. Additionally, a variety of biochemical means of enriching for products containing adaptor 2 are possible such as using affinity probes that are complementary to the hairpin loop sequence itself. Product I results in the same SMI sequence in both the Read 1 and Read 2 sequence reads. In the example depicted above, Product I sequences can thus be identified by virtue of having matching SMIs of the form XXXX in Read 1 and XXXX in Read 2.

By contrast, in the case of Product II, the SMI sequences on either end of the sequenced molecule will arise from distinct DCS adaptors having different SMI sequences. In the example shown above, Product II sequences yield SMIs of the form XXXX (Read 1)-BBB (Read 2) upon sequencing of the top strand, and BBBB (Read 1)-XXXX (Read 2) upon sequencing of the bottom strand. Thus Product II sequences can be easily identified and computationally removed from the final sequence data.

Data resulting from Product II is useful, because Product II corresponds to the product analyzed under the approach detailed in the Example below. Product I contains a self-complementary hairpin sequence that can impair polymerase extension during amplification, however, this type of amplification has already been enabled in the technique of "Hairpin PCR" [50] which involves linking of the two strands followed by amplification with gene-specific primers. Amplification conditions that are compatible with amplification of hairpin DNA are thus already established. Moreover, ligation and amplification with circularizing "linkers" (i.e. hairpin linkers affixed to both ends of a fragment) has been demonstrated as a step in the Pacific Biosciences sample preparation workflow [49]. As the sequence of the linker itself does not matter in the workflow, the published linker sequences from either of these references would be adequate for use in the assay.

In some aspects of some embodiments, deliberate ligation of "U-shaped" adaptors or hairpin linkers containing 1) a double-stranded n-mer (or other form of degenerate or semi-degenerate double-stranded tag as enumerated above) plus 2) primer binding sites to both ends of a captured fragment may be desireable. Producing closed circles of captured material may help facilitate removal of non-captured DNA by exonuclease digestion given that circularized DNA will be protected from digestion by such enzymes. Additionally, closed circles may be pre-amplified using rolling circle amplification or serve as the substrate for continuous loop sequencing [49]. Recognition sites for restriction endonuclease digestion could be engineered into these adaptors to render closed loops open once again if more convenient for subsequent steps.

In another embodiment, flow cell sequences or PCR binding sites, again denoted as FC1 and FC2, may be included in both the PCR primers and the hairpin linker adaptor, as well as a ligatable sequence on the end of the hairpin linker (denoted as L below). The hairpin linker adaptor may additionally include one or more cleavable sequences, denoted as R in the example below (the R may be any appropriate restriction enzyme target sequence, or any other cleavable sequence). Such a hairpin linker design is shown below:

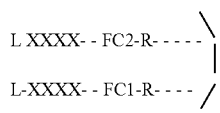

The target DNA with ligation site denoted as L is as follows:
---------------DNA--------L
---------------DNA'-------L Following ligation of the linker, the product may be amplified with PCR primers as follows:

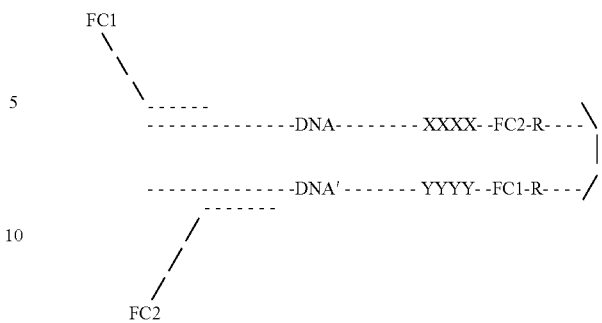

The resultant product will be of the form:
FC1--------DNA--------XXXX--FC2-R-----R-FC1--YYYY--------DNA'-------FC2

After amplification of the product, the cleavage sites R may be cleaved to result in the following sequencable products:
FC1--------DNA--------XXXX--FC2
and
FC1--YYYY--------DNA'-------FC2

These products may then be sequenced directly. This design has the advantage of allowing for targeted sequencing of a specific region of the genome, and furthermore avoids the need to sequence a hairpin product, as sequencing of a hairpin will be less efficient due to the self-complementarity present within the hairpin molecule.

Single-Stranded SMI Sequences

In one embodiment, a single-stranded SMI sequence is incorporated into the single-stranded portion of the hairpin loop (regions of sequence complementarity are denoted as "="). The SMI sequence is shown as four nucleotides in length in the following examples, but in practice an Nmer of any length, including approximately 3 to 20 nucleotides, will suffice.

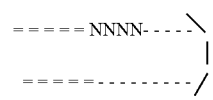

Ligation of the hairpin linker and a Y-shaped sequencing adaptor (with PCR primer binding sites labeled as FC1 and FC2) yields the following product:

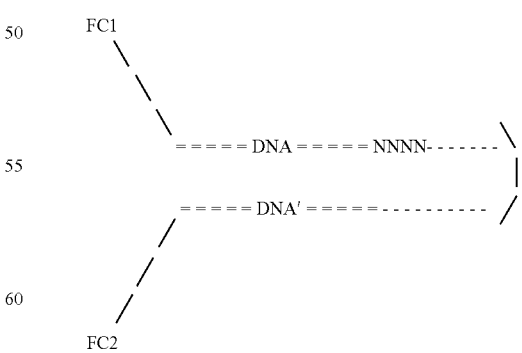

Melting and PCR amplification of this product yields the following DNA product:
FC1-------DNA-----NNNN------hairpin sequence------DNA'-------FC2

Following PCR duplication of the product and formation of consensus reads based upon the shared SMI sequence among all the PCR duplicates, the sequences of the two strands (denoted DNA and DNA') can then be compared to form a duplex consensus sequence.

In another embodiment, a single-stranded SMI is incorporated into a modified "Y-shaped" sequencing adaptor in which PCR primer binding sites are located at the sites labeled FC1 and FC2 (regions of sequence complementarity are depicted as "=")

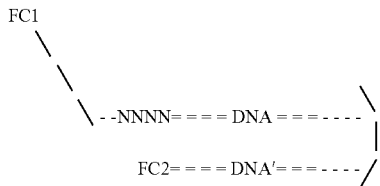

It will be apparent to one skilled in the art that a single-stranded SMI sequence tag can be located in any of several positions within either the sequencing adaptor or the hairpin linker. The single-stranded SMI sequence tag can be synthesized as a random oligonucleotide sequence, or can be sequenced as a set of fixed sequences by synthesis on an array, or by any other suitable method known in the art.

Methods for Synthesis of Complementary or Partially Complementary Double Stranded SMI Tags SMI adaptors molecules containing a double-stranded, complementary, degenerate or semi-degenerate SMI tag can be made by any of a number of methods, including copying of a single-stranded SMI sequence by a DNA polymerase as described above or synthesis and annealing of two oligonucleotides containing complementary SMI sequences. An additional method involves synthesizing a set of linear oligonucleotides which will self-anneal into the appropriate form. Inclusion of a cleavable linker in each oligonucleotide will then allow for conversion of a "hairpin shaped" SMI adaptor molecule into a "Y-shaped" SMI adaptor molecule. For example, an oligonucleotide may be prepared of the following form:

In this schematic, X and Y represent complementary nucleotides, and U indicates a cleavable linker, such as uracil (which can be cleaved by combined treatment with uracil DNA glycosylase and apurinic endonuclease), although any other cleavable linker will suffice. The oligonucleotide may be designed with appropriate regions of self-complementarity to anneal into the following form:

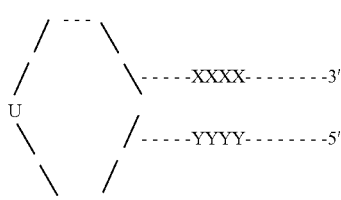

The linker (e.g. uracil) may then be cleaved, yielding a DCS adaptor:

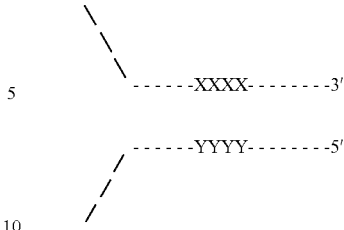

A double-stranded SMI hairpin linker can be constructed by an analogous method but without the need for a cleavable linker. For example, a set of nucleotides of known sequence where X and Y represent the complementary SMI sequences can be synthesized on an array, or by any other suitable method known in the art:

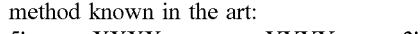

This oligonucleotide can then self-anneal to form a hairpin linker with complementary SMI sequences.

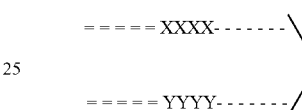

Any of the oligonucleotides described above can also include any ligatable sequence as overhangs on either the 5' or 3' end, or can be used for blunt end ligation.

DCS SMI Adaptor Molecules May Include Sequences to Allow for Targeted DNA Capture DCS SMI adaptor molecules contain ligatable ends to allow attachment of the adaptor to a target DNA molecule. In some embodiments, the ligatable end may be complementary to a DNA overhang on the target DNA, for example, one generated by digestion of target DNA with a restriction endonuclease. Selective ligation of the adaptor to the targeted DNA containing the matching Single-stranded overhanging DNA sequence will then allow for partial purification of the targeted DNA. A non-limiting example of this embodiment is shown above. In some embodiments, the DCS SMI adaptor molecule, or a hairpin linker SMI adaptor molecule, may additionally contain modifications such as biotin to facilitate affinity purification of target DNA that has ligated to the adaptor.

In another embodiments, specific PCR primers can selectively amplify specific regions of genome when the adaptor that is ligated to the other end of the molecule is a hairpin (or "U-shape"). Alternatively, this method may be used with or without the need for this cleavable hairpin sequence.

Preparation of DNA for Duplex Consensus Sequencing May be Performed by PCR Amplification in a Hairpin Structure Another embodiment involves fragmentation of DNA at defined regions, for example by treatment of DNA with a site-specific restriction endonuclease or a mixture of such endonucleases, followed by annealing of a hairpin oligonucleotide linker, and amplification of the hairpin complex with PCR primers sufficient for amplification of the desired DNA sequence. Annealing of the hairpin linker to only one of the two ends of the DNA duplex could be accomplished by using different restriction enzymes to cut on either end of the target duplex, and then having the hairpin linker ligation adaptor being ligatable to only one of the two resultant ligatable ends.

The example shown below indicates forward and reverse PCR primers (labeled 1 and 2) in conjunction with a hairpin linker to allow linked amplification of both complementary strands of duplex DNA. Such amplification, in conjunction with a single-stranded or double-stranded SMI sequence, would allow for targeted amplification and high accuracy deep sequencing of a specific sequence of interest. In the schematic shown below, a single-stranded SMI sequence is incorporated into PCR primer FC1. It would be apparent to one skilled in the art that the SMI sequence could also be incorporated in primer FC2, or in the hairpin linker.

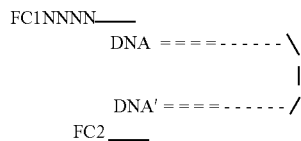

Amplified Product:
FC1NNNN DNA----hairpin sequence----DNA'FC2

This product can then be subjected to consensus sequencing analysis. The SMI sequence allows one to group together products of PCR amplification arising from a single molecule of duplex DNA. The sequences of the two DNA strands can then be compared for error correction.

Uses of SMI Adapter Molecules

The SMI adaptor molecules described herein have several uses. In some embodiments, the SMI adaptor molecules described herein may be used in methods to obtain the sequence or other sequence-related information of a double-stranded target nucleic acid molecule. According to the embodiments described herein, the term "double-stranded target nucleic acid molecule" includes a double-stranded DNA molecule or a double-stranded RNA molecule. Thus, the SMI adaptor molecules and methods of use described herein are applicable to genotyping and other applications related to sequencing of DNA molecules, but are also applicable to RNA sequencing applications such as for sequencing of double-stranded RNA viruses. Methods for sequencing RNA may include any of the embodiments described herein with respect to DNA sequencing, and vice-versa. For example, any double stranded target nucleic acid molecule may be ligated to an SMI adaptor molecule which includes a double-stranded RNA or DNA n-mer tag and an RNA or DNA ligation adapter as described above. Methods exist for directly sequencing RNA [51]; alternatively, the ligated product may be reverse transcribed into DNA, and then sequenced as a double-stranded target DNA molecule.

In one embodiment, the double-stranded target nucleic acid molecule may be a sheared double-stranded DNA or RNA fragment. The sheared target DNA or RNA molecule may be end repaired and a double-stranded target nucleic acid sequence ligation adaptor may be added to each end of the sheared target DNA or RNA molecule. The double-stranded target nucleic acid sequence ligation adaptor may be any suitable ligation adaptor that is complementary to the SMI ligation adaptor described above including, but not limited to a T-overhang, an A-overhang, a CG overhang, blunt end or any other ligatable sequence. In some embodiments, the double-stranded target nucleic acid sequence ligation adaptor may be made using a method for A-tailing or T-tailing with polymerase extension; adding an overhang with a different enzyme; using a restriction enzyme to create a ligatable overhang; or any other method known in the art.

Methods to obtain the sequence or other sequence-related information of a double-stranded target nucleic acid molecule may include a step of ligating the double-stranded target nucleic acid molecule to at least one SMI adaptor molecule, such as those described above, to form a double-stranded target nucleic acid complex. In one embodiment, each end of the double-stranded target nucleic acid molecule is ligated to an SMI adaptor molecule. The double-stranded target nucleic acid complex is then amplified by a method known in the art (e.g., a PCR or non-PCR method known in the art), resulting in a set of uniquely labeled, amplified SMI-target nucleic acid products. These products are then sequenced using any suitable method known in the art including, but not limited to, the Illumina sequencing platform, ABI SOliD sequencing platform, Pacific Biosciences sequencing platform, 454 Life Sciences sequencing platform, Ion Torrent sequencing platform, Helicos sequencing platform, and nanopore sequencing technology.

In certain embodiments, a method of generating an error corrected double-stranded consensus sequence is provided. Such a method, also referred to as duplex consensus sequencing (DCS), allows for a quantitative detection of sites of DNA damage. DCS analysis facilitates the detection of DNA damage signatures, in that single stranded DNA mutations that are not present in the complementary strand can be inferred to be artifactual mutations arising from damaged nucleotides. Not only can one correct for these erroneous mutations, but the ability to indirectly infer that damage is present on the DNA could be a useful biomarker (e.g. for cancer risk, cancer metabolic state, mutator phenotype related to defective damage repair, carcinogen exposure, chronic inflammation exposure, individual-specific aging, neurodegenerative diseases etc). The ability to use different polymerases during the first round(s) of PCR to mis-incorporate at damage sites could potentially add even more information. Besides polymerases, other DNA modifying/repair enzymes could be used prior to amplification to convert damage of one sort that doesn't give a specific mutagenic signature into another sort that does with whatever polymerase is used. Alternatively, DNA modifying/repair enzymes could be used to remove damaged bases, and one could sequence both strands of DNA both with and without the enzymatic treatment. Mutations in single-stranded DNA that are seen to be removed by the enzymatic treatment can thus be inferred to be arising due to DNA damage. This could be useful on human nuclear or mtDNA but also might also be useful with model organisms (mice, yeast, bacteria etc), treated with different new damaging agents, facilitating a screen for DNA damaging compounds that would be analogous to the widely used Ames test [52].

The method of generating an error corrected double-stranded consensus sequence may include a first stage termed "single strand consensus sequencing" (SSCS) followed by a second stage of duplex consensus sequencing (DCS). Therefore, the method includes steps of tagging individual duplex DNA molecules with an SMI adaptor molecule, such as those described above; generating a set of PCR duplicates of the tagged DNA molecules by performing a suitable PCR method; creating a single strand consensus sequence from all of the PCR duplicates which arose from an individual molecule of single-stranded DNA. Each DNA duplex should result in two single strand consensus sequences. The work through these three steps conclude the first stage and is termed SSCS.

The method of generating an error corrected double-stranded consensus sequence further comprises the second stance that is termed DCS. The DCS stage includes steps of comparing the sequence of the two single strand consensus sequences arising from a single duplex DNA molecule, and further reducing sequencing or PCR errors by considering only sites at which the sequences of both single-stranded DNA molecules are in agreement. The method that includes the first stage and the second stage termed Duplex Consensus Sequencing (DCS).

The step of tagging of both strands of individual duplex DNA may be accomplished by ligation of degenerate or semi-degenerate complementary DNA sequences; as the complementary nature of the two strands of such a tag sequence allows the two molecules to be grouped together for error correction. Alternatively, as described above, the two duplex DNA strands may be linked by ligation of a U-shaped SMI adaptor molecule, and the two DNA strands can thus both be tagged with a single-stranded SMI tag.

In the method described above, a set of sequenced SMI-DNA products generated in the methods described above may be grouped into families of paired target nucleic acid strands based on a common set of SMI sequences. Then, the paired target nucleic acid strands can be filtered to remove nucleotide positions where the sequences seen on both of the paired partner DNA strands are not complementary. This error corrected double-stranded consensus sequence may be used in a method for confirming the presence of a true mutation (as opposed to a PCR error or other artifactual mutation) in a target nucleic acid sequence. According to certain embodiments, such a method may include identifying one or more mutations present in the paired target nucleic acid strands that have one or more nucleotide positions that disagree between the two strands, then comparing the mutation present in the paired target nucleic acid strands to the error corrected double-stranded consensus sequence. The presence of a true mutation is confirmed when the mutation is present on both of the target nucleic acid strands and also appear in all members of a pared target nucleic acid family.

The accuracy of current approaches to next-generation sequencing is limited due to their dependence on interrogating single-stranded DNA. This dependence makes potential sources of error such as PCR amplification errors and DNA damage fundamentally limiting. However, the complementary strands of a double-stranded DNA molecule (or "DNA duplex") contain redundant sequencing information (i.e., one molecule reciprocally encoding the sequence information of its partner) which can be utilized to eliminate such artifacts. Limitations related to sequencing single-stranded DNA (e.g., sequencing errors) may therefore be overcome using the methods described herein. This is accomplished by individually tagging and sequencing each of the two strands of a double-stranded (or duplex) target nucleic acid molecule and comparing the individual tagged amplicons derived from one half of a double-stranded complex with those of the other half of the same molecule. Duplex Consensus Sequencing (DCS), significantly lowers the error rate of sequencing. In some embodiments, the DCS method may be used in methods for high sensitivity detection of rare mutant and variant DNA as described further below.

As described above, one approach that has previously been reported for DNA sequencing involves incorporation of a random tag sequence into a PCR primer [36]. This approach results in an improvement in accuracy relative to standard Illumina sequencing, but is fundamentally limited in that it is based upon amplification and sequencing of single-stranded DNA and thus cannot overcome limitations in sensitivity owing to single-stranded DNA damage events. In the methods described herein, PCR duplicates are generated from a single strand of DNA, and the sequences of the duplicates are compared. Mutations are scored only when they are present in multiple replicates of a single starting molecule. The DCS approach overcomes the limitation of previous approaches by considering both DNA strands.

DNA damage should not be a limiting factor in DCS, because miscoding damage events at a single base-pair position occur essentially exclusively on only one of the two DNA strands. For DNA damage to result in an artifactual mutation in DCS, damage would need to be present at the same nucleotide position on both strands. Even if complementary nucleotides in a duplex were both damaged, the damage would need to result in complementary sequencing errors to result in mis-scoring of a mutation. Likewise, spontaneous PCR errors would need to result in complementary mutations at the same position on both strands; with a first-round mutation frequency of Taq polymerase of approximately $10^{-5}$ and three possible incorrect bases that could be mis-inserted, the probability of two complementary PCR errors occurring would be $10^{\times 5} \times 10^{-5} \times 1/3 = 3.3 \times 10^{-11}$ According to some embodiments, the sequencing method may be performed using the Illumina or similar platforms including those enumerated above without the use of SMI adaptor molecules, but instead by using the random shear points of DNA as identifiers. For a given DNA sequence seen in sequencing read 1 with a specific set of shear points, the partner strand will be seen as a matching sequence in read two with identical shear points. In practice, this approach is limited by the limited number of possible shear points that overlap any given DNA position. However, according to some embodiments, shear points of a target nucleic acid molecule may be used as unique identifiers to identify double-stranded (or duplex) pairs, resulting in an apparent error frequency at least as low as that seen with traditional sequencing methods, but with a significantly lower loss of sequence capacity. In other embodiments, DCS based on shear points alone may have a role for confirmation that specific mutations of interest are true mutations which were indeed present in the starting sample (i.e. present in both DNA strands), as opposed to being PCR or sequencing artifacts. Overall, however, DCS is most generally applicable when randomized, complementary double-stranded SMI sequences are used. A 24 nucleotide double-stranded SMI sequence was used in the Example described below, which may yield up to $4^{24} = 2.8 \times 10^{14}$ distinct double-stranded SMI sequences. Combining information regarding the shear points of DNA with the SMI tag sequence would allow a shorter SMI to be used, thus minimizing loss of sequencing capacity due to sequencing of the SMI itself.

In certain embodiments, the SMI adaptor molecules may also be used in methods of single-molecule counting for accurate determination of DNA or RNA copy number [38]. Again, since the SMI tags are present in the adaptors, there are no altered steps required in library preparation, which is in contrast to other methods for using random tags for single-molecule counting. Single-molecule counting has a large number of applications including, but not limited to, accurate detection of altered genomic copy number (e.g., for sensitive diagnosis of genetic conditions such as trisomy 21 [47]), for accurate identification of altered mRNA copy number in transcriptional sequencing and chromatin immunoprecipitation experiments, quantification of circulating microRNAs, quantification of viral load of DNA or RNA viruses, quantification of microorganism abundance, quantification of circulating neoplastic cells, counting of DNA-labeled molecules of any variety including tagged antibodies or aptamers, and quantification of relative abundances of different individual's genomes in forensic applications.

In another embodiment, the SMI adaptor molecules may be used in methods for unambiguous identification of PCR duplicates. In order to restrict sequencing analysis to uniquely sequenced DNA fragments, many sequencing studies include a step to filter out PCR duplicates by using the shear points at the ends of DNA molecules to identify distinct molecules. When multiple molecules exhibit identical shear points, all but one of the molecules are discarded from analysis under the assumption that the molecules represent multiple PCR copies of the same starting molecule. However sequence reads with identical shear points can also reflect distinct molecules because there are a limited number of possible shear points at any given genomic location, and with increasing sequencing depth, recurrent shear points are increasingly likely to be seen [48]. Because the use of SMI tags (or "double-stranded SMI sequences") allows every molecule to be uniquely labeled prior to PCR duplication, true PCR duplicates may be unambiguously identified by virtue of having a common (i.e., the same or identical) SMI sequence. This approach would thereby minimize the loss of data by overcoming the intrinsic limitations of using shear points to identify PCR duplicates.

Importantly, once SMI-containing adaptors are synthesized by a straightforward series of enzymatic steps or are produced through synthesis of a set of oligonucleotides containing complementary tag sequences, they may be substituted for standard sequencing adaptors. Thus, use of DCS does not require any significant deviations from the normal workflow of sample preparation for Illumina DNA sequencing. Moreover, the DCS approach can be generalized to nearly any sequencing platform because a double-stranded SMI tag can be incorporated into other existing adaptors, or for sequencing approaches that do not require adaptors, a double-stranded SMI tag can be ligated onto duplex DNA sample prior to sequencing. The compatibility of DCS with existing sequencing workflows, the potential for greatly reducing the error rate of DNA sequencing, and the multitude of applications for the double-stranded SMI sequences validate DCS as a technique that may play a general role in next generation DNA sequencing.

The following examples are intended to illustrate various embodiments of the invention. As such, the specific embodiments discussed are not to be construed as limitations on the scope of the invention. It will be apparent to one skilled in the art that various equivalents, changes, and modifications may be made without departing from the scope of invention, and it is understood that such equivalent embodiments are to be included herein. Further, all references cited in the disclosure are hereby incorporated by reference in their entirety, as if fully set forth herein.

EXAMPLES

Example 1

Generation of SMI Adaptor Molecules and Their Use in Sequencing Double-Stranded Target DNA Materials and Methods Materials. Oligonucleotides were from IDT and were ordered as PAGE purified. Klenow exo- was from NEB. T4 ligase was from Enzymatics.

DNA isolation. Genomic DNA was isolated from normal human colonic mucosa by sodium iodide extraction (Wako Chemicals USA).

Adaptor synthesis. The adaptors were synthesized from two oligos, designated as:

```
the primer strand:
                                    (SEQ ID NO: 1)
AATGATACGGCGACCACCGAGATCTACACTCTTTCCCTACACGACGCTCT TCCGATCT;
and the template strand:
                                    (SEQ ID NO: 2)
/5phos/ACTGNNNNNNNNNNNNNAGATCGGAAGAGCACACGTCTGAACTC

CAGTCAC.
```

The two adaptor strands were annealed by combining equimolar amounts of each oligo to a final concentration of 50 micromolar and heating to 95° C. for 5 minutes. The oligo mix was allowed to cool to room temperature for over 1 hour. The annealed primer-template complex was extended in a reaction consisting of 40 micromolar primer-template, 25 units Klenow exo-DNA polymerase (New England Biolabs), 250 micromolar each dNTP, 50 mM NaCl, 10 mM Tris-HCl pH 7.9, 10 mM MgCl$_2$, and 1 mM dithiothreitol (DTT) for 1 hour at 37° C. The product was isolated by ethanol precipitation. Due to the partial A-tailing property of Klenow exo-, this protocol results in a mixture of blunt-ended adapters and adapters with a single-nucleotide A hverhang. A single-nucleotide A overhang was added to residual blunt fragments by incubating the adapters with 25 units Klenow exo-, 1 mM dATP, 50 mM NaCl, 10 mM Tris-HCl pH 7.9, 10 mM MgCl2, and 1 mM dithiothreitol (DTT) for 1 hour at 37° C. The product was again ethanol precipitated and resuspended to a final concentration of 50 micromolar.

Sequencing library preparation. 3 micrograms of DNA was diluted into 130 microliters of TE buffer (10 mM tris-HCl, pH 8.0, 0.1 M EDTA) and was sheared on the Covaris AFA system with duty cycle 10%, intensity 5, cycles/burst 200, time 20 seconds×6, temperature 4° C. DNA was purified with 2 volumes of Agencourt AMPure XP beads per the manufacturer's protocol. After end-repair with the NEB end-repair kit per the manufacturer's protocol, DNA fragments larger than the optimal range of ~200-500 bp were removed by adding 0.7 volumes of AMPure XP beads and transferring the supernatant to a separate tube (fragments larger than 500 bp bind to the beads and are discarded). An additional 0.65 volumes of AMPure XP beads were added (this step allows fragments of approximately 200 bp or greater to bind to the beads). The beads were washed and DNA eluted. DNA was then T-tailed in a reaction containing 5 units Klenow exo-, 1 mM dTTP, 50 mM NaCl, 10 mM Tris-HCl pH 7.9, 10 mM MgCl2, 1 mM. The reaction proceeded for 1 hour at 37 C. DNA was purified with 1.2 volumes of AMPure XP beads. The custom adaptors were ligated by combining 750 ng of T-tailed DNA with 250 pmol adaptors in a reaction containing 3000 units T4 DNA ligase, 50 mM Tris-HCl pH 7.6, 10 mM MgCl2, 5 mM DTT, 1 mM ATP. The reaction was incubated 25 C for 15 minutes, and purified with 1.2 volumes of AMPure XP beads.

Pre-capture amplification. 375 ng adaptor-ligated DNA was PCR amplified with primers AATGATACGGCGAC-CACCGAG (SEQ ID NO:3) and GTGACTGGAGTTCA- GACGTGTGC (SEQ ID NO:4) using the Kappa high-fidelity PCR kit for 8 cycles with an annealing temperature of 60 C. The product was purified with 1.2 volumes of AMPure XP beads.

DNA capture. Target capture was performed with the Agilent SureSelect system per the manufacturer's recommendations, except that capture volumes were performed at one-half of the standard volume. The capture set targeted an arbitrary 758 kb region of the genome consisting of both coding and noncoding sequences. Capture baits were 120 nt in length, and were prepared with the Agilent eArray tool with 3× tiling.

Post-capture amplification. Captured DNA was amplified with PCR primers AATGATACGGCGACCACCGAG (SEQ ID NO:3) and CAAGC AGAAGACGGCAT-ACGAGATXXXXXXGTGACTGGAGTTCA-GACGTGTGC (SEQ ID NO:5) where XXXXXX indicates the position of a fixed multiplexing barcode sequence). 20 fmol of DNA was used per lane for sequencing on an Illumina HiSeq 2000.

Data processing. Reads with intact SMI adaptors include a 12 nucleotide random sequence, followed by a 5 nucleotide fixed sequence. These reads were identified by filtering out reads that lack the expected fixed sequence at positions 13-17. The SMI sequence from both the forward and reverse sequencing reads (i.e., the first and second degenerate n-mer sequences) was computationally added to the read header, and the fixed sequence removed. The first 4 nucleotides located following the adaptor sequence were also removed due to the propensity for ligation and end-repair errors to result in an elevated error rate near the end of the DNA fragments. Reads having common (i.e., identical) SMI sequences were grouped together, and were collapsed to generate a consensus read. Sequencing positions were discounted if the consensus group covering that position consisted of fewer than 3 members, or if fewer than 90% of the sequences at that position in the consensus group had the identical sequence. Reads were aligned to the human genome with the Burrows-Wheeler Aligner (BWA). The consensus sequences were then paired with their strand-mate by grouping each 24 nucleotide tag of form AB in read 1 with its corresponding tag of form BA in read 2. Resultant sequence positions were considered only when information from both DNA strands was in perfect agreement. An overview of the data processing workflow is as follows:
1. Discard reads that do not have the 5 nt fixed reference (or "spacer") sequence (CAGTA; SEQ ID NO:6) present after 12 random nucleotides.
2. Combine the 12 nt SMI tags from read 1 and read 2, and transfer the combined 24 nt SMI sequence into the read header.
3. Discard SMIs with inadequate complexity (i.e., those with >10 consecutive identical nucleotides).
4. Remove the 5 nt fixed reference sequence.
5. Trim an additional 4 nt from the 5' ends of each read pair (sites of error prone end repair).
6. Group together reads which have identical 24 nt SMIs.
7. Collapse to SMI consensus reads, scoring only positions with 3 or more SMI duplicates and >90% sequence identity among the duplicates.
8. For each read in read 1 file having SMI of format Aft group with corresponding DCS partner in read 2 with SMI of format BA.
9. Only score positions with identical sequence among both DCS partners. 10. Align reads to the human genome.
Code for carrying out the workflow may be pre-existing or may involve programming within the skill of those in the art.

In some embodiments, however, the Python code, which is illustrated in FIG. 10, may be used for carrying out the pairing and scoring of partner strands according to steps 8 and 9 of the workflow described above.

Overview

Figure 1:
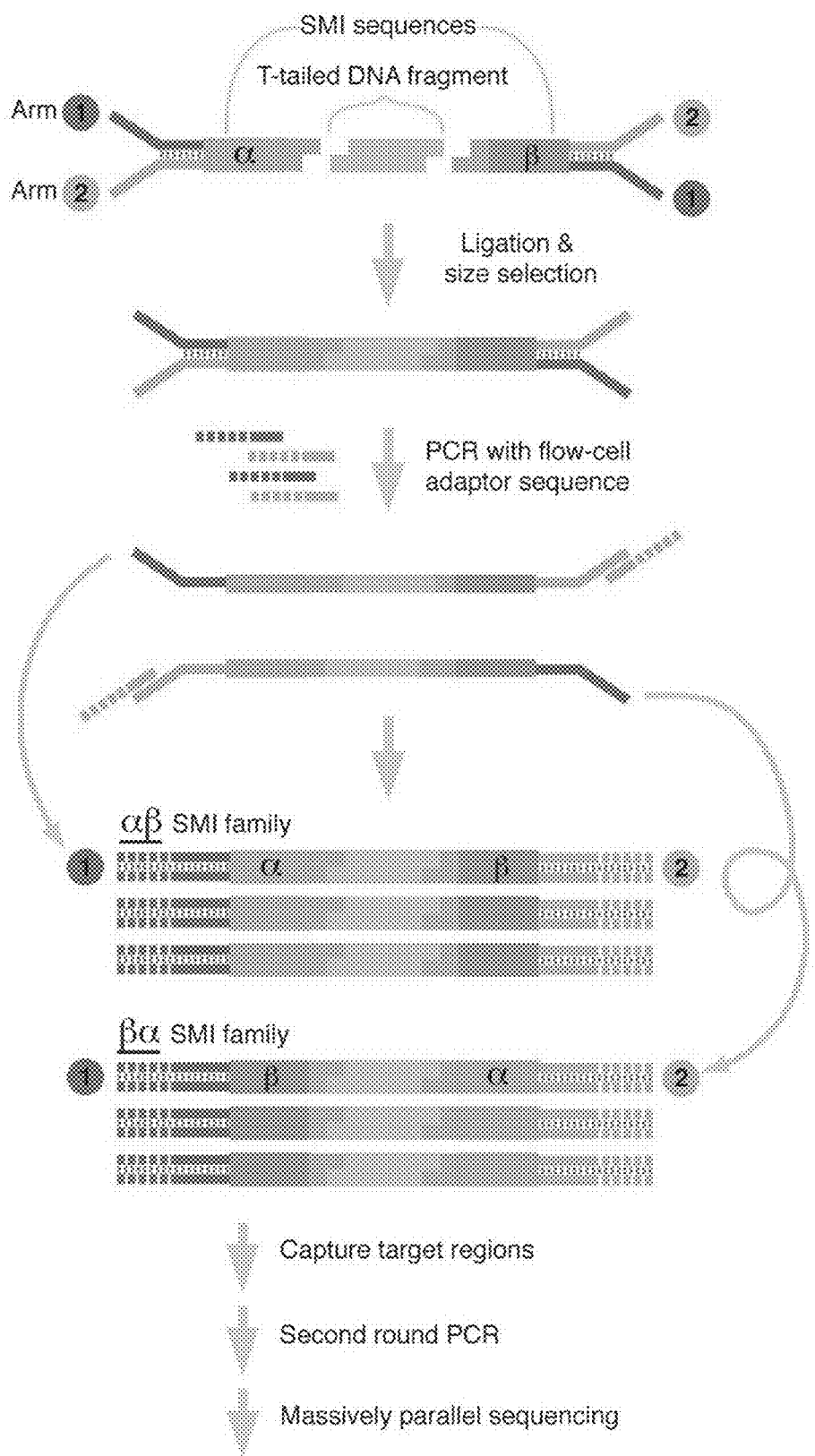
FIG. 1 illustrates an overview of Duplex Consensus Sequencing. Sheared double-stranded DNA that has been end-repaired and T-tailed is combined with A-tailed SMI adaptors and ligated according to one embodiment. Because every adaptor contains a unique, double-stranded, complementary n-mer random tag on each end (n-mer=12 bp according to one embodiment), every DNA fragment becomes labeled with two distinct SMI sequences (arbitrarily designated α and β in the single capture event shown). After size-selecting for appropriate length fragments, PCR amplification with primers containing Illumina flow-cell-compatible tails is carried out to generate families of PCR duplicates. By virtue of the asymmetric nature of adapted fragments, two types of PCR products are produced from each capture event. Those derived from one strand will have the α SMI sequence adjacent to flow-cell sequence 1 and the β SMI sequence adjacent to flow cell sequence 2. PCR products originating from the complementary strand are labeled reciprocally.

To overcome limitations in the sensitivity of variant detection by single-stranded next-generation DNA sequencing, an alternative approach to library preparation and analysis was designed, which is known herein as Duplex Consensus Sequencing (DCS) (FIG. 1). The DCS method described herein involves tagging both strands of duplex DNA with a random, yet complementary double-stranded nucleotide sequence, which is known herein as a double-stranded single molecule identifier (SMI) sequence. The SMI sequences (in this case, double stranded SMI sequences) are incorporated into the SMI adaptor molecules by introducing a single-stranded randomized nucleotide sequence into one adapter strand and the extending the opposite strand with a DNA polymerase to yield a complementary, double-stranded SMI sequence (FIG. 2). The individually tagged strands are then PCR amplified. Every duplicate that arises from a single strand of DNA will have the same SMI, and thus each strand in a DNA duplex pair generates a distinct, yet related population of PCR duplicates after amplification owing to the complementary nature of the SMIs on the two strands of the duplex. Comparing the sequence obtained from each of the two strands comprising a single molecule of duplex DNA facilitates differentiation of sequencing errors from true mutations. When an apparent mutation is, due to a PCR or sequencing error, the substitution will only be seen on a single strand. In contrast, with a true DNA mutation, complementary substitutions will be present on both strands (see FIG. 4C).

Following tagging with a double-stranded SMI and PCR amplification, a family of molecules is obtained that arose from a single DNA molecule; members of the same PCR "family" are then grouped together by virtue of having a common (i.e., the same) SMI tag sequence. The sequences of uniquely tagged PCR duplicates are subsequently compared in order to create a PCR consensus sequence. Only DNA positions that yield the same DNA sequence in a specified proportion of the PCR duplicates in a family, such as 90% of the duplicates in one embodiment, are used to create the PCR consensus sequence. This step filters out random errors introduced during sequencing or PCR to yield the PCR consensus sequences, each of which derives from an individual molecule of single-stranded DNA. This set of PCR consensus sequences are called single strand consensus sequences (SSCSs).

Figure 3:
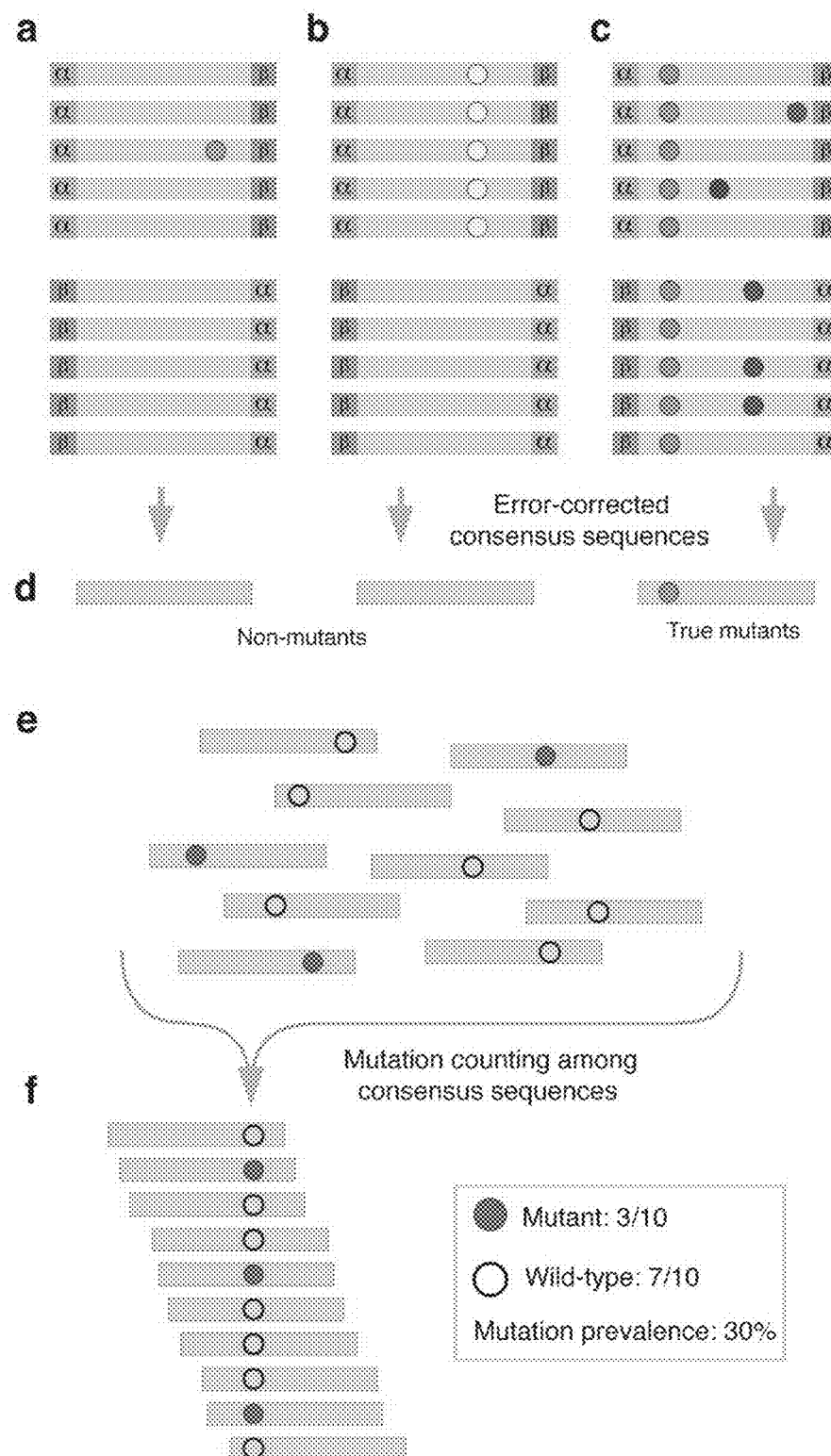
FIG. 3 illustrates error correction through Duplex Consensus Sequencing (DCS) analysis according to one embodiment. (a-c) shows sequence reads (brown) sharing a unique set of SMI tags are grouped into paired families with members having strand identifiers in either the αβ or βα orientation. Each family pair reflects one double-stranded DNA fragment. (a) shows mutations (spots) present in only one or a few family members representing sequencing mistakes or PCR-introduced errors occurring late in amplification. (b) shows mutations occurring in many or all members of one family in a pair representing mutations scored on only one of the two strands, which can be due to PCR errors arising during the first round of amplification such as might occur when copying across sites of mutagenic DNA damage. (c) shows true mutations (* arrow) present on both strands of a captured fragment appear in all members of a family pair. While artifactual mutations may co-occur in a family pair with a true mutation, these can be independently identified and discounted when producing (d) an error-corrected consensus sequence (i.e., single stranded consensus sequence) (+arrow) for each duplex. (e) shows consensus sequences from all independently captured, randomly sheared fragments containing a particular genomic site are identified and (f) compared to determine the frequency of genetic variants at this locus within the sampled population.

Next, PCR consensus sequences arising from two complementary strands of duplex DNA can be identified by virtue of the complementary SMIs (FIG. 3) to identify the "partner SMI." Specifically, a 24-nucleotide SMI consists of two 12-nucleotide sequences that can be designated XY. For an SMI of form XY in read 1, the partner SMI will be of form YX in read 2. An example to illustrate this point is given in FIG. 4. Following partnering of two strands by virtue of their complementary SMIs, the sequences of the strands are compared. Sequence reads at a given position are kept only if the read data from each of the two paired strands is in agreement.

Results

In order to label or tag each of the strands of duplex DNA with unique complementary tags, adaptors which contain the standard sequences required for the Illumina HiSeq system were synthesized, but with addition of a double-stranded, complementary SMI sequence (or "tag") of 12 random nucleotides (or a random "degenerate sequence") per strand. Target DNA molecules having a random SMI sequence n-mer that is 12 nucleotides in length on each end will therefore have a unique 24 nucleotide SMI sequence. The adaptors were prepared (FIG. 2) from two partially complementary oligonucleotides, one of which has a single-stranded 12 nucleotide random nucleotide sequence (i.e. a first random degenerate nucleotide n-mer sequence) followed by a single stranded fixed reference sequence that is 4 nucleotides in length. The single-stranded random nucleotide tag was converted to a double-stranded, complementary SMI tag by extension with Klenow exo- DNA polymerase and the extended adaptor was purified by ethanol precipitation. Due to the partial A-tailing property of Klenow exo-, this protocol results in a mixture of blunt-ended adaptors and adaptors with a single-nucleotide A overhang (data not shown). A single-nucleotide A-overhang was added to the residual blunt fragments by incubating the adaptors with Klenow exo- DNA polymerase and a high concentration of dATP (1 mM), and purified the adaptors again by ethanol precipitation.

DNA for sequencing was sheared and end-repaired by standard methods, with size-selection for fragments in the range of ~200-500 bp by size-selective binding to Ampure XP beads. Standard Illumina library preparation protocols involve ligating A-tailed DNA to T-tailed adaptors. However, because A-tailed adaptors were used, the DNA was T-tailed by incubating the end-repaired DNA with Klenow exo- DNA polymerase and 1 mM dTTP. The adaptor-ligated library was PCR amplified and subjected to SureSelect capture, with targeting of an arbitrary 758 kb portion of the genome (DNA coordinates available upon request). The efficiency of adaptor ligation, PCR amplification, DNA capture, and sequencing were comparable to those seen with standard library preparation methods (data not shown). Although Agilent Sure Select probes are used in this example, any suitable method of DNA selection may be used to capture particular target double-stranded DNA sequences. For example, selection and capture may be accomplished by any selection by hybridization method (e.g., Agilent SureSelect, Primer Extension Capture, exploitation of biotinylated PCR amplicons as bait, Agilent HaloPlex) wherein probes that target the desired double-stranded DNA sequence may be recovered by an in-array capture (using probes immobilized on glass slides) or by affinity using magnetic beads in an in-solution capture. In addition, mitochondrial and some other forms of DNA may be isolated by size selection. Alternatively, in some embodiments, no enrichment is performed.

This protocol was used to sequence DNA isolated from normal colonic mucosa. Mutations were initially scored without consideration of the SMI sequences. PCR duplicates were filtered out with samtools rmdup, a standard tool which uses the shear points of DNA molecules to identify PCR duplicates, as molecules arising from duplicated DNA will have shared shear points. In order to focus specifically on non-clonal mutations, only those positions in the genome with at least 20× coverage and at which fewer than 5% of reads differed from the hg19 reference sequence were considered. This approach resulted in 70.9 million nucleotides of sequence data and 56,890 mutations, indicating an overall mutation frequency of $8.03 \times 10^{-4}$, in accord with the error rate of Illumina next-generation sequencing of ~0.1-1% [32].

Next, the SMI tags were used to group together PCR duplicates that arose from individual single-stranded DNA molecules and to create a consensus sequence from the family of duplicates. At least 3 PCR duplicates were required, with at least 90% agreement in sequence among all duplicates, to consider a site for mutations. Scoring the mutation frequency as above, again considering only sites with a minimum of 20× coverage and with <5% of reads differing from reference, resulted in 145 million nucleotides of sequence with 6,508 mutations and an overall mutation frequency of $4.47 \times 10^{-5}$, consistent with prior reports [36]. Notably, far more nucleotides of DNA sequence were obtained in this approach (145 million) than in the standard Illumina sequencing approach (70 million) detailed above which is dependent on use of the shear points of single-ended reads to identify PCR duplicates. The improved sequence coverage arose from use of the SMI to identify PCR duplicates, because identifying PCR duplicates by consideration of uniquely sheared DNA ends is fundamentally limited by the small number of possible shear points that overlap a given position of the genome and the propensity for specific genomic regions to be more readily undergo shearing. Thus filtering PCR duplicates by using shear points resulted in discarding a large portion of the reads.

Finally, the complementary nature of the double-stranded SMI sequences was used to identify pairs of consensus groups that arose from complementary DNA strands. Sequence reads were considered only when the read data from each of the two strands is in perfect agreement. In a pilot experiment, after grouping of PCR duplicates as above, 29,409 SMI partner pairs were found, indicative that fewer than 1% of tags had their corresponding partner tag present in the library. The low recovery of tag pairs was most likely due to inadequate amplification of the starting DNA library. Among these tag-pairs, 24,772 duplex consensus strands were identified with an average strand length of 82 nucleotides, resulting in 2 million nucleotides of DNA consensus sequence. The sequences of the paired duplex strands disagreed at 3,585 of the nucleotide positions, indicative of single-stranded errors (i.e. PCR or sequencing errors); these sites of disagreement were removed, leaving only bases at which the sequence of both duplex strands were in perfect agreement. Next, as above, analysis of mutation frequencies was restricted to sites with at least 10× coverage and at which fewer than 10% of reads disagreed from the hg19 reference sequence. Because the 2 million nucleotides of read data were spread across a 758kb target, our average depth was only ~3×. Thus only 14,464 nucleotides of DNA sequence corresponded to sites with at least 10× depth. Among these sites, zero mutations were seen. To increase the number of tag pairs considered, analysis described above was repeated, but PCR duplicates were grouped with a minimum of only 1 duplicate per site. This resulted in 28,359 nucleotides of DNA sequence with at least 10× depth. Again, no mutations were detected.

Current experiments are being performed on vastly smaller target DNA molecules (ranging from ~300 bp to ~20 kb in size). Use of smaller DNA targets will allow for much greater sequencing depth, and far more accurate assessment of the background mutation rate of the assay. In addition, the protocol has been modified to incorporate a greater number of PCR cycles initiated off a smaller number of genome equivalents, which will increase the fraction of tags for which both of the partner tag strands have been sufficiently amplified to be represented in the final sequence data. Indeed, among the 3.6 million SMIs present in our initial library which underwent PCR duplication, 1.5 million of the SMIs were present only once, indicating insufficient amplification of the DNA due in part to the low number of PCR cycles used.

Example 2

Duplex Sequencing of Human Mitochondrial DNA

Materials and Methods

In addition to those described in Example 1 above, the following materials and methods were also used.

DNA Isolation. Mitochondrial DNA was isolated as previously described (4).

Data processing. The entire human genome sequence (hg19) was used as reference for the mitochondrial DNA experiment, and reads that mapped to chromosomal DNA were removed. Reads sharing identical tag sequences were then grouped together and collapsed to consensus reads. Sequencing positions were discounted if the consensus group covering that position consisted of fewer than three members or if fewer than 90% of the sequences at that position in the consensus group had the identical sequence. A minimum group size of three was selected because next-generation sequencing systems have an average base calling error rate of ~$\frac{1}{100}$. Requiring the same base to be identified in three distinct reads decreases the frequency of single-strand consensus sequence (SSCS) errors arising from base-call errors to $(\frac{1}{100})3=1\times10^{-6}$, which is below the frequency of spontaneous PCR errors that fundamentally limit the sensitivity of SSCSs. The requirement for 90% of sequences to agree to score a position is a highly conservative cutoff. For example, with a group size of eight, a single disagreeing read will lead to 87.5% agreement and the position will not be scored. If all groups in an experiment are of size nine or less, this cutoff will thus require perfect agreement at any given position to score the position. Further development of our protocol may allow for less stringent parameters to be used to maximize the number of SSCS and duplex consensus sequence (DCS) reads that can be obtained from a given experiment.

Results

Figure 5:
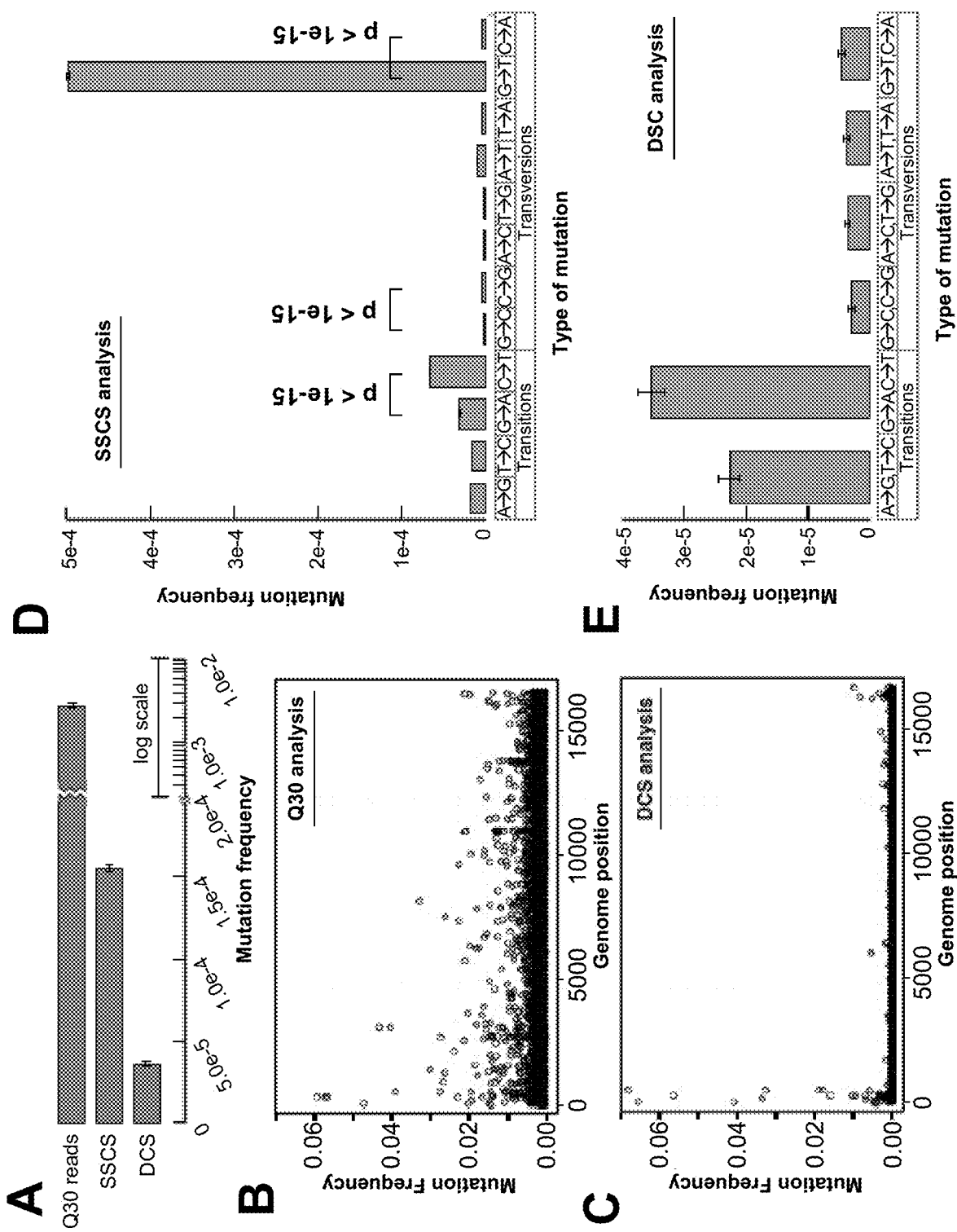
FIG. 5 illustrates duplex sequencing of human mitochondrial DNA. (A) Overall mutation frequency as measured by a standard sequencing approach, SSCS, and DCS. (B) Pattern of mutation in human mitochondrial DNA by a standard sequencing approach. The mutation frequency (vertical axis)

Having established the methodology for Duplex Sequencing with M13mp2 DNA, which is a substrate for which the mutation frequency and spectrum are fairly well established, it was desired to apply the approach to a human DNA sample. Thus, mitochondrial DNA was isolated from human brain tissue and sequenced the DNA after ligation of Duplex Sequencing adapters. A standard sequencing approach with quality filtering for a Phred score of 30 resulted in a mutation frequency of $2.7\times10^{-3}$, and SSCS analysis yielded a mutation frequency of $1.5\times10^{-4}$. In contrast, DCS analysis revealed a much lower overall mutation frequency of $3.5\times10^{-5}$ (FIG. 5A). The frequency of mutations in mitochondrial DNA has previously been difficult to measure directly due in part to sources of error in existing assays that can result in either overestimation or underestimation of the true value. An additional confounder has been that most approaches are limited to interrogation of mutations within a small fraction of the genome [56]. The method of single-molecule PCR, which has been proposed as an accurate method of measuring mitochondrial mutation frequency [56] and is considered resistant to damage-induced background errors [57], has resulted in a reported mitochondrial mutation frequency in human colonic mucosa of $5.9\times10^{-5}\pm3.2\times10^{-5}$ [56], which is in excellent agreement with our result. Likewise, mitochondrial DNA sequence divergence rates in human pedigrees are consistent with a mitochondrial mutation frequency of $3-5\times10^{-5}$ [58, 59].

When the distribution of mutations throughout the mitochondrial genome is considered, the quality filtered reads (analyzed without consideration of the tags) have many artifactual errors, such that identification of mutational hotspots is difficult or impossible (FIG. 5B). DCS analysis removed these artifacts (FIG. 5C) and revealed striking hypermutability of the region of replication initiation (D loop), which is consistent with prior estimates of mutational patterns in mitochondrial DNA based upon sequence variation at this region within the population [60].

SSCS analysis produced a strong mutational bias, with a 130-fold excess of G→T relative to C→A mutations (FIG. 5D), consistent with oxidative damage of the DNA leading to first-round PCR mutations as a significant source of background error. A high level of oxidative damage is expected in mitochondrial DNA, due to extensive exposure of mitochondria to free radical species generated as a byproduct of metabolism [61]. DCS analysis (FIG. 5E) removed the mutational bias and revealed that transition mutations are the predominant replication errors in mitochondrial DNA. The DCS mutation spectrum is in accord with prior estimates of deamination events [62] and T-dGTP mispairing by the mitochondrial DNA polymerase [63] as primary mutational forces in mitochondrial DNA. Furthermore, the mutation spectrum of our mitochondrial data are consistent with previous reports of heteroplasmic mutations in human brain showing an increased load of A→G/T→C and G→A/C→T transitions, relative to transversions [64, 65]. A similar spectral bias has also been reported in mice [62, 66] and in population studies of Drosophila melanogaster [67].

Example 3

Demonstration of Error-Correction by DCS Using Randomly Sheared DNA Ends as Single Molecule Identifiers Materials and Methods In addition to those described in the Examples above, the following materials and methods were also used to demonstrate the capability of DCS analysis to remove sequencing errors Sequencing library preparation. Genomic DNA was isolated from a derivative of Saccharomyces cerevisiae strain SC288 by standard methods. The DNA was randomly sheared by the Covaris AFA system, followed by end-repair, A-tailing, and ligation of Illumina TruSeq DNA sequencing adaptors, all by standard library preparation methods. The resultant sequence data consisted of an average 32.5 fold depth of the 12 megabase S. cerevisiae genome.

Data analysis. The first 10 nucleotides of each sequencing read pair, corresponding to the randomly sheared DNA ends, were combined, such that the first 10 nucleotides of read 1, referred to as A, was combined with the first 10 nucleotides of read 2, referred to as B, to yield an SMI tag of form AB. Reads were grouped according to SMI sequence, and nucleotide reads were considered only if they agreed among at least 90% of family members sharing a given tag sequence. For DCS analysis, a tag of form AB1 is partnered with the corresponding tag of form BA2, and nucleotide positions are considered only when the sequence is in agreement among read pairs with matching tags AB1 and BA2.

Results

In order to demonstrate the capability of DCS analysis to remove sequencing errors, a sequencing library was prepared under standard conditions with commercially available sequencing adaptors, and the randomly sheared DNA ends were used as SMI's. First, reads were grouped by SMI with a minimum family size of 1 member. Considering only sites with a minimum of 20× coverage and with <5% of reads differing from reference, this analysis resulted in 644.8 million nucleotides of sequence data and 2,381,428 mutations, yielding an overall mutation frequency of $3.69 \times 10^{-3}$.

The data was then subjected to DCS analysis with the SMI tags, searching for tags of form AB1 that have partner tags of form BA2, and considered only positions at which the sequence from the two strands was in perfect agreement. 3.1% of the tags had a matching partner present in the library, resulting in 2.9 million nucleotides of sequence data. The sequences of the duplex strands were not complementary at 40,874 nucleotide positions; these disagreeing positions, representing likely sequencing or PCR errors, were removed from analysis. Again considering positions with at least 20× coverage and <5% of reads differing from reference, 3.0 million nucleotides of sequence data and 157 mutations were obtained, with an overall mutation frequency of $5.33 \times 10^{-5}$, indicative of removal of >98% of mutations seen in raw analysis and thereby demonstrating the capability of DCS to lower the error rate of DNA sequencing.

To compare this result to the method of Kinde et al. [36], reads were grouped into families by SMI tag as before but filtered for families with a minimum of 3 members. This resulted in 1.4 million nucleotides of sequence data and 61 mutations, with an overall mutation frequency of $4.25 \times 10^{-5}$. Thus, the method of Kinde et al., with a minimum family size of 3, resulted in less than half as much resultant sequence data after filtering than was obtained by DCS with a minimum family size of 1. Thus, DCS lowered the error rate of sequencing to a comparable degree to a method considered state-of-the-art, but with less loss of sequencing capacity.

Discussion

It was demonstrated that DCS analysis, using sheared DNA ends as unique molecular identifiers, results in a lowering of the apparent error rate of DNA sequencing. As this proof-of-concept experiment was performed on a library that was not optimized to maximize recovery of both strands, there were not sufficient strand-pairs recovered to perform DCS analysis with a minimum family size of >1 member. Requiring family sizes >1 is expected to further reduce sequencing errors. Moreover, this analysis was limited in that it did not include ligation of degenerate SMI tag sequences; owing to the limited number of shear points flanking any given nucleotide position, use of shear points as SMIs limits the number of unique molecules that can be sequenced in a single experiment. The use of shear points as SMIs in conjunction with an exogenously ligated SMI tag sequence would allow for increased depth of sequencing at any given nucleotide position.

Example 4

Demonstrations of Duplex Consensus Sequencing

In addition to those described in Examples 1 and 2 above, the following materials and methods were also used.

Materials and Methods

Construction of M13mp2 Variants. M13mp2 gapped DNA encoding the LacZ α fragment was extended by human DNA polymerase δ[2] and the resultant products were transformed into *Escherichia coli* and subjected to blue-white color screening as previously described [3]. Mutant plaques were sequenced to determine the location of the mutation resulting in the color phenotype. A series of mutants, each differing from wild type by a single nucleotide change, were then mixed together with wild-type M13mp2 DNA to result in a single final mixture with distinct mutants represented at ratios of 1/10 (G6267A), 1/100 (T6299C), 1/1,000 (G6343A), and 1/10,000 (A6293T).

Oxidative Damage of M13mp2 DNA. Induction of DNA damage was performed by minor modifications to a published protocol [5]: 300 ng of M13mp2 double-stranded DNA was incubated in 10 mM sodium phosphate buffer, pH 7.0, in the presence of 10 μM iron sulfate and 10 μM freshly diluted hydrogen peroxide. Incubation proceeded for 30 min at 37° C. in open 1.5-mL plastic microcentrifuge tubes.

DNA Isolation. M13mp2 DNA was isolated from *E. coli* strain MC1061 by Qiagen Miniprep. To allow for greater sequencing depth at a defined region of the M13mp2 genome, an 840-bp fragment was enriched by complete digestion with the restriction enzymes Bsu36I and NaeI (New England Biolabs), followed by isolation of the fragment on an agarose gel by the Recochip system (Takara Bio).

Duplex Consensus Sequencing of M13 DNA Removes Artifactual Sequencing Errors

The spontaneous mutation rate of M13mp2 DNA has been well established by a number of exquisitely sensitive genetic assays to be 3.0E-6 [53], that is, an average of one spontaneous base substitution error for every 330,000 nucleotides. Thus this substrate is well suited as a control for determining the background error frequency of DNA sequencing. M13mp2 DNA was sheared and ligated to adaptors containing double-stranded complementary SMI sequences by standard protocols, and was subjected to deep sequencing on an Illumina HiSeq 2000 followed by Consensus Sequencing analysis (FIG. 6).

Analysis of the data by standard methods (i.e., without consideration of the double stranded SMI sequences) resulted in an error frequency of 3.8E-03, more than one thousand fold higher than the true mutation frequency of M13mp2 DNA. This indicates that >99.9% of the apparent mutations identified by standard sequencing are in fact artifactual errors.

The data were then analyzed by Single Strand Consensus Sequencing (SSCS), using the unique SMI tag affixed to each molecule to group PCR products together in order to create a consensus of all PCR products that came from an individual molecule of single-stranded DNA. This resulted in a mutation frequency of 6.4E-O5, suggesting that ~98% of sequencing errors are corrected by SSCS.

Next, the data were subjected to Duplex Consensus Sequencing (DCS), which further corrects errors by using the complementary SMI tags to compare the DNA sequence arising from both of the two strands of a single molecule of duplex DNA. This approach resulted in a mutation frequency of 2.5E-06, in nearly perfect agreement with the true mutation frequency of M13mp2 DNA of 3.0E-06. The number of nucleotides of DNA sequence obtained by a standard sequencing approach, and after SSCS and DCS analysis, may be found in Table 1 below.

TABLE 1

Data yield from Duplex Sequencing

|  | M13mp2 DNA | Mitochondrial DNA |
|---|---|---|
| Initial nucleotides | $6.5 \times 10^9$ | $6.2 \times 10^9$ |
| SSCS nucleotides | $8.7 \times 10^7$ | $4.1 \times 10^8$ |
| DCS nucleotides | $2.2E \times 10^7$ | $9.7 \times 10^7$ |
| Initial reads per SSCS read | 75 | 15 |
| Initial reads per DCS read | 295 | 64 |
| SSCS reads per DCS read | 4 | 4 |

Initial nucleotides represent raw reads that contain the expected fixed adapter sequence following 12 degenerate nucleotides and map to the reference genome. Apparent nucleotide loss in converting initial reads to SSCSs occurs because many of the initial reads intentionally represent identical PCR duplicates of single-stranded DNA molecules to allow for removal of sequencing and PCR errors by comparison of the sequence among the duplicates. A minimum of three initial reads are required to produce one SSCS; however, a greater average number is necessary to ensure that most DNA fragments have at least this number of duplicates. Under fully optimized conditions, each DCS read would arise from exactly two SSCS reads (one arising from each strand of the initial molecule of duplex DNA). An SSCS:DCS ratio greater than 2 indicates that the strand partner of some SSCSs was not recovered.

For an artifactual error to be scored by DCS, complementary artifactual errors must occur on both strands of a molecule of duplex DNA. Thus the background (artifactual) error frequency of DCS may be calculated as: (probability of error on one strand)*(probability of error on other strand)*(probability that both errors are complementary).

As the background error frequency of SSCS in this experiment was –6E-S, the background error frequency of DCS can be calculated as 6E-S*6E-S*(⅓)=1.2E-9. This represents a greater than 3 million fold improvement over the error rate of 3.5E-03 that was obtained by a standard sequencing approach.

Consensus Sequencing Reveals Likely Sites of DNA Damage

M13mp2 DNA was sequenced as detailed above, with DCS adaptors containing double-stranded complementary SMIs. The spectrum of mutations obtained with SSCS was determined. Data was filtered to consist of forward-mapping reads from Read 1, i.e. sequencing of the reference strand, and reverse-mapping reads from Read 1, i.e. sequencing of the anti-reference strand. True mutations would result in an equal balance between mutations on the reference strand and their complementary mutation on the anti-reference strand.

However, SSCS analysis revealed a large number of single-stranded GT mutations on reads mapping in the forward orientation to the reference genome, with a much smaller number of CA mutations mapping to the reverse orientation. The spectrum of mutations identified by both SSCS and DCS analysis were examined relative to literature reference values [53] for the M13mp2 substrate (FIG. 7A). SSCS analysis revealed a large excess of G→A/C→T and G→T/C→A mutations relative to reference (P<10-6, two-sample t test). In contrast, DCS analysis was in excellent agreement with the literature values with the exception of a decrease relative to reference of these same mutational events: G→A/C→T and G→T/C→A (P<0.01). To probe the potential cause of these spectrum deviations, the SSCS data were filtered to consist of forward-mapping reads from read 1 (i.e., direct sequencing of the reference strand) and the reverse complement of reverse-mapping reads from read 1 (i.e., direct sequencing of the antireference strand.) True double-stranded mutations should result in an equal balance of complementary mutations observed on the reference and antireference strand. However, SSCS analysis revealed a large number of single-stranded G→T mutations, with a much smaller number of C→A mutations (FIG. 7B). A similar bias was seen with a large excess of C→T mutations relative to G→A mutations.

Base-specific mutagenic DNA damage is a likely explanation of these imbalances. Excess G→T mutations are consistent with the oxidative product 8-oxo-guanine (8-oxo-G) causing first round PCR errors and artifactual G→T mutations. DNA polymerases, including those commonly used in PCR, have a strong tendency to insert adenine opposite 8-oxo-G [45, 54], and misinsertion of A opposite 8-oxo-G would result in erroneous scoring of a G→T mutation. Likewise, the excess C→T mutations are consistent with spontaneous deamination of cytosine to uracil [47], a particularly common DNA damage event that results in insertion during PCR of adenine opposite uracil and erroneous scoring of a C→T mutation.

To determine whether the excess G→T mutations seen in SSCSs might reflect oxidative DNA damage at guanine nucleotides, before sequencing library preparation M13mp2 DNA was incubated with the free radical generator hydrogen peroxide in the presence of iron, a protocol that induces DNA damage [55]. This treatment resulted in a substantial further increase in G→T mutations by SSCS analysis (FIG. 8A), consistent with PCR errors at sites of DNA damage as the likely mechanism of this biased mutation spectrum. In contrast, induction of oxidative damage did not alter the mutation spectrum seen with DCS analysis (FIG. 8B), indicating that duplex consensus sequences are not similarly susceptible to DNA damage artifacts.

Furthermore, relative to the literature reference values, DCS analysis results in a lower frequency of G→T/C→A and C→T/G→A mutations (FIG. 7A), which are the same mutations elevated in SSCS analysis as a probable result of DNA damage. Notably, the M13mp2 LacZ assay, from which reference values have been derived, is dependent upon bacterial replication of a single molecule of M13mp2 DNA. Thus, the presence of oxidative damage within this substrate could cause an analogous first-round replication error by *Escherichia coli*, converting a single-stranded damage event into a fixed, double-stranded mutation during replication. The slight reduction in the frequency of these two types of mutations measured by DCS analysis may, therefore, reflect the absence of damage-induced errors that are scored by the in vivo LacZ assay.

Consensus Sequencing Accurately Recovers Spiked-In Control Mutations

A series of M13mp2 variants were constructed which contain known single base substitutions. These variants were then mixed together at known ratios, and the mixture was prepared for sequencing with DCS adaptors with double-stranded complementary SMIs and was sequenced on an Illumina HiSeq 2000. The data was then analyzed by consensus sequencing (FIG. 9). With conventional analysis of the data (i.e. without consideration of the SMI tags), variants present at a level of <1/100 could not be accurately identified. This limitation occurs because at any given position, artifactual mutations are seen at a level of nearly 1/100.

In contrast, when the data is analyzed by Single Strand Consensus Sequencing (SSCS) with ~20,000 fold depth, accurate recovery of mutant sequence is seen down to one mutant molecule per 10,000 wild type molecules. Duplex Consensus Sequencing (DCS), which was not performed on this sample, would allow for detection of even rarer mutations.

REFERENCES

The references, patents and published patent applications listed below, and all references cited in the specification above are hereby incorporated by reference in their entirety, as if fully set forth herein.

[1] Metzker ML. Sequencing technologies—the next generation. Nat Rev Genet. 2010; 11:31-46.

[2] Shendure J, Ji H. Next-generation DNA sequencing. Nat Biotechnol. 2008; 26:1135-45.

[3] Lecroq B, Lejzerowicz F, Bachar D, Christen R, Esling P, Baerlocher L, et al. Ultra-deep sequencing of foraminiferal microbarcodes unveils hidden richness of early monothalamous lineages in deep-sea sediments. Proc Natl Acad Sci USA. 2011; 108:13177-82.

[4] Mackelprang R, Waldrop M P, DeAngelis K M, David M M, Chavarria K L, Blazewicz S J, et al. Metagenomic analysis of a permafrost microbial community reveals a rapid response to thaw. Nature. 2011; 480:368-71.

[5] Garcia-Garcerà M, Gigli E, Sanchez-Quinto F, Ramirez O, Calafell F, Civit S, et al. Fragmentation of contaminant and endogenous DNA in ancient samples determined by shotgun sequencing; prospects for human palaeogenomics. PLoS ONE. 2011; 6:e24161.

[6] Fordyce S L, Ávila-Arcos M C, Rockenbauer E, Børsting C, Frank-Hansen R, Petersen F T, et al. High-throughput sequencing of core STR loci for forensic genetic investigations using the Roche Genome Sequencer FLX platform. BioTechniques. 2011; 51:127-33.

[7] Druley T E, Vallania F L M, Wegner D J, Varley K E, Knowles O L, Bonds J A, et al. Quantification of rare allelic variants from pooled genomic DNA. Nat Methods. 2009; 6:263-5.

[8] Out A A, van Minderhout I J H M, Goeman J J, Ariyurek Y, Ossowski S, Schneeberger K, et al. Deep sequencing to reveal new variants in pooled DNA samples. Hum Mutat. 2009; 30:1703-12.

[9] Fan H C, Blumenfeld Y J, Chitkara U, Hudgins L, Quake S R. Noninvasive diagnosis of fetal aneuploidy by shotgun sequencing DNA from maternal blood. Proc Natl Acad Sci USA. 2008; 105:16266-71.

[10] Chiu R W K, Akolekar R, Zheng Y W L, Leung T Y, Sun H, Chan K C A, et al. Noninvasive prenatal assessment of trisomy 21 by multiplexed maternal plasma DNA sequencing: large scale validity study. BMJ. 2011; 342:c7401.

[11] Mitchell P S, Parkin R K, Kroh E M, Fritz B R, Wyman S K, Pogosova-Agadjanyan E L, et al. Circulating microRNAs as stable blood-based markers for cancer detection. Proc Natl Acad Sci USA. 2008; 105:10513-8.

[12] Ding L, Ley T J, Larson D E, Miller C A, Koboldt D C, Welch J S, et al. Clonal evolution in relapsed acute myeloid leukaemia revealed by whole-genome sequencing. Nature. 2105; 481:506-9.

[13] Boyd S D, Marshall E L, Merker J D, Maniar J M, Zhang L N, Sahaf B, et al. Measurement and Clinical Monitoring of Human Lymphocyte Clonality by Massively Parallel V-D-J Pyrosequencing. Science Translational Medicine. 2009; 1:12ra23-12ra23.

[14] Hyman R W, Herndon C N, Jiang H, Palm C, Fukushima M, Bernstein D, et al. The dynamics of the vaginal microbiome during infertility therapy with in vitro fertilization-embryo transfer. J Assist Reprod Genet. 2012; 29:105-15.

[15] LaTuga M S, Ellis J C, Cotton C M, Goldberg R N, Wynn J L, Jackson R B, et al. Beyond bacteria: a study of the enteric microbial consortium in extremely low birth weight infants. PLoS ONE. 2011; 6:e27858.

[16] Minot S, Sinha R, Chen J, Li H, Keilbaugh S A, Wu G D, et al. The human gut virome:interindividual variation and dynamic response to diet. Genome Res. 2011; 21:1616-25.

[17] Yang J, Yang F, Ren L, Xiong Z, Wu Z, Dong J, et al. Unbiased parallel detection of viral pathogens in clinical samples by use of a metagenomic approach. J Clin Microbiol. 2011; 49:3463-9.

[18] Nasu A, Marusawa H, Ueda Y, Nishijima N, Takahashi K, Osaki Y, et al. Genetic heterogeneity of hepatitis C virus in association with antiviral therapy determined by ultra-deep sequencing. PLoS ONE. 2011; 6:e24907.

[19] Campbell P J, Pleasance E D, Stephens P J, Dicks E, Rance R, Goodhead I, et al. Subclonal phylogenetic structures in cancer revealed by ultra-deep sequencing. Proc Natl Acad Sci USA. 2008; 105:13081-6.

[20] De Grassi A, Segala C, Iannelli F, Volorio S, Bertario L, Radice P, et al. Ultradeep Sequencing of a Human Ultraconserved Region Reveals Somatic and Constitutional Genomic Instability. PLoS Biol. 2010; 8:e1000275.

[21] Zagordi O, Klein R, Däumer M, Beerenwinkel N. Error correction of next-generation sequencing data and reliable estimation of HIV quasispecies. Nucleic Acids Research. 2010; 38:7400-9.

[22] Wang C, Mitsuya Y, Gharizadeh B, Ronaghi M, Shafer R W. Characterization of mutation spectra with ultra-deep pyrosequencing: application to HIV-1 drug resistance. Genome Res. 2007; 17:1195-201.

[23] Carlson C A, Kas A, Kirkwood R, Hays L E, Preston B D, Salipante S J, et al. Decoding cell lineage from acquired mutations using arbitrary deep sequencing. Nat Methods. 2012; 9:78-80.

[24] He Y, Wu J, Dressman D C, Iacobuzio-Donahue C, Markowitz S D, Velculescu V E, et al. Heteroplasmic mitochondrial DNA mutations in normal and tumour cells. Nature. 2010; 464:610-4.

[25] Ameur A, Stewart J B, Freyer C, Hagström E, Ingman M, Larsson N-G, et al. Ultra-Deep Sequencing of Mouse Mitochondrial DNA: Mutational Patterns and Their Origins. PLoS Genet. 2011; 7:e1002028.

[26] Kanagawa T. Bias and artifacts in multitemplate polymerase chain reactions (PCR). J Biosci Bioeng. 2003; 96:317-23.

[27] Meyerhans A, Vartanian J P, Wain-Hobson S. DNA recombination during PCR. Nucleic Acids Research. 1990; 18:1687-91.

[28] Quail M A, Kozarewa I, Smith F, Scally A, Stephens P J, Durbin R, et al. A large genome center's improvements to the Illumina sequencing system. Nat Methods. 2008; 5:1005-10.

[29] Salk J, Fox E, Loeb L. Mutational heterogeneity in human cancers: origin and consequences. Annual Review of Pathology. 2009; 5:51-75.

[30] Kozarewa I, Ning Z, Quail M A, Sanders M J, Berriman M, Turner D J. Amplification-free Illumina sequencing-library preparation facilitates improved mapping and assembly of (G+C)-biased genomes. Nat Methods. 2009; 6:291-5.

[31] Vandenbroucke I, Van Marck H, Verhasselt P, Thys K, Mostmans W, Dumont S, et al. Minor variant detection in amplicons using 454 massive parallel pyrosequencing: experiences and considerations for successful applications. BioTechniques. 2011; 51:167-77.

[32] Flaherty P, Natsoulis G, Muralidharan O, Winters M, Buenrostro J, Bell J, et al. Ultrasensitive detection of rare mutations using next-generation targeted resequencing. Nucleic Acids Research. 2012; 40:e2-e.

[33] Shen Y, Wa n Z, Coarfa C, Drabek R, Chen L, Ostrowski E A, et al. A SNP discovery method to assess variant allele probability from next-generation resequencing data. Genome Res. 2010; 20:273-80.

[34] Miner B E, Stöger R J, Burden A F, Laird C D, Hansen R S. Molecular barcodes detect redundancy and contamination in hairpin-bisulfite PCR. Nucleic Acids Research. 2004; 32:e135.

[35] McCloskey M L, Stöger R, Hansen R S, Laird C D. Encoding PCR products with batch-stamps and barcodes. Biochem Genet. 2007; 45:761-7.

[36] Kinde I, Wu J, Papadopoulos N, Kinzler K W, Vogelstein B. Detection and quantification of rare mutations with massively parallel sequencing. Proc Natl Acad Sci USA. 2011; 108:9530-5.

[37] Jabara C B, Jones C D, Roach J, Anderson J A, Swanstrom R. Accurate sampling and deep sequencing of the HIV-1 protease gene using a Primer ID. Proc Natl Acad Sci USA. 2011; 108:20166-71.

[38] Kivioja T, Vähärautio A, Karlsson K, Bonke M, Enge M, Linnarsson S, et al. Counting absolute numbers of molecules using unique molecular identifiers. Nat Methods. 2011; 9:72-4.

[39] Casbon J A, Osborne R J, Brenner S, Lichtenstein C P. A method for counting PCR template molecules with application to next-generation sequencing. Nucleic Acids Research. 2011; 39:e81-e.

[40] Shiroguchi K, Jia T Z, Sims P A, Xie X S. Digital RNA sequencing minimizes sequence-dependent bias and amplification noise with optimized single-molecule barcodes. Proc Natl Acad Sci USA. 2012; 109:1347-52.

[41] Fu G K, Hu J, Wang P-H, Fodor S P A. Counting individual DNA molecules by the stochastic attachment of diverse labels. Proc Natl Acad Sci USA. 2011; 108:9026-31.

[42] Cervantes R B, Stringer J R, Shao C, Tischfield J A, Stambrook P J. Embryonic stem cells and somatic cells differ in mutation frequency and type. Proc Natl Acad Sci USA. 2002; 99:3586-90.

[43] Lindahl T, Wood R D. Quality control by DNA repair. Science. 1999; 286:1897-1905.

[44] Kunkel, T A. Mutational specificity of depurination. Proc Natl Acad Sci USA. 1984; 81:1494-98.

[45] Shibutani S, Takeshita M, Grollman A P. Insertion of specific bases during DNA synthesis past the oxidation-damaged base 8-oxodG. Nature. 1991; 349:431-4.

[46] Stiller M, Green R E, Ronan M, Simons J F, Du L, He W., et al. Patterns of nucleotide misincorporations during enzymatic amplification and direct large-scale sequencing of ancient DNA. Proc Natl Acad Sci USA. 2006; 103: 13578-84.

[47] Ehrich M, Deciu C, Zwiefelhofer T, Tynan J A, Cagasan L, Tim R, et al. Noninvasive detection of fetal trisomy 21 by sequencing of DNA in maternal blood: a study in a clinical setting. Am J Obsbet Gynecol. 2011; 204:205e1-11.

[48] Bainbridge M N, Wang M, Burgess D L, Kovar C, Rodesch M, D'Ascenzo M, et al. Whole exome capture in solution with 3 Gbp of data. Genome Biol. 2010; 11:R62: 1-8.

[49] Travers K J, Chin C S, Rank D R, Eid J S, Turner S W. A flexible and efficient template format for circular consensus sequencing and SNP detection. Nucleic Acids Res. 2010; 38:159e1---8.

[50] Kaur M, Makrigiorgos G M. Novel amplification of DNA in a hairpin structure: towards a radical elimination of PCR errors from amplified DNA. Nucleic Acids Res. 2003; 31:26e1---7.

[51] Ozsolak, F., Platt, A. R., Jones, D. R., Reifenberger, J. G., Sass, L. E., McInerney, P., Thompson, J. F., Bowers, J., Jarosz, M., and Milos, P. M. (2009). Direct RNA sequencing. Nature 461, 814-818.

[52] Lynch A M, Sasaki j C, Elespuru R, Jacobson-Kram D, Thybaud V, et al. New and emerging technologies for genetic toxicity testing. Environ Mol Mutagen. 2011; 52(3): 205-23.

[53] Thomas D C, Roberts J D, Sabatino R D, Myers T W, et al. Fidelity of mammalian DNA replication and replicative DNA polymerases. Biochemistry. 1991; 30:11751-9.

[54] Kasai H, et al. (1993) Formation, inhibition of formation, and repair of oxidative 8-hydroxyguanine DNA damage. Basic Life Sci 61:257-262.

[55] McBride T J, Preston B D, Loeb L A (1991) Mutagenic spectrum resulting from DNA damage by oxygen radicals. Biochemistry 30:207-213.

[56] Greaves L C, et al. (2009) Quantification of mitochondrial DNA mutation load. Aging Cell 8:566-572.

[57] Kraytsberg Y, Nicholas A, Caro P, Khrapko K (2008) Single molecule PCR in mtDNA mutational analysis: Genuine mutations vs. damage bypass-derived artifacts. Methods 46:269-273.

[58] Howell N, Kubacka I, Mackey D A (1996) How rapidly does the human mitochondrial genome evolve? Am J Hum Genet 59:501-509.

[59] Parsons T J, et al. (1997) A high observed substitution rate in the human mitochondrial DNA control region. Nat Genet 15:363-368.

[60] Stoneking M (2000) Hypervariable sites in the mtDNA control region are mutational hotspots. Am J Hum Genet 67:1029-1032.

[61] Kennedy S R, Loeb L A, Herr A J (2011) Somatic mutations in aging, cancer and neurodegeneration. Mech Ageing Dev.

[62] Vermulst M, et al. (2007) Mitochondrial point mutations do not limit the natural lifespan of mice. Nat Genet 39:540-543.

[63] Song S, et al. (2005) DNA precursor asymmetries in mammalian tissue mitochondria and possible contribution to mutagenesis through reduced replication fidelity. Proc Natl Acad Sci USA 102:4990-4995.

[64] Lin M T, Simon D K, Ahn C H, Kim L M, Beal M F (2002) High aggregate burden of somatic mtDNA point mutations in aging and Alzheimer's disease brain. Hum Mol Genet 11:133-145.

[65] Jazin E E, Cavelier L, Eriksson I, Oreland L, Gyllensten U (1996) Human brain contains high levels of heteroplasmy in the noncoding regions of mitochondrial DNA. Proc Natl Acad Sci USA 93:12382-12387.

[66] Khaidakov M, Heflich R H, Manjanatha M G, Myers M B, Aidoo A (2003) Accumulation of point mutations in mitochondrial DNA of aging mice. Mutat Res 526: 1-7.

[67] Haag-Liautard C, et al. (2008) Direct estimation of the mitochondrial DNA mutation rate in Drosophila melanogaster. PLoS Biol 6:e204.

What is claimed is:

1. A method of sequencing DNA comprising:

preparing a sequencing library from a sample comprising a plurality of double-stranded DNA fragments, wherein preparing the sequence library comprises ligating adapter molecules to the plurality of double-stranded DNA fragments to generate a plurality of double-stranded adapter-DNA molecules;

sequencing first and second strands of the adapter-DNA molecules to provide a first strand sequence read derived from an original first strand and a distinct, yet related second strand sequence read derived from an original second strand for individual adapter-DNA molecules in the plurality;

for at least some of the adapter-DNA molecules:

comparing the first strand sequence read with the distinct, yet related second strand sequence read; and generating a consensus sequence of the double-stranded DNA fragment wherein each position in the consensus sequence is identified as correct if the particular position in the first strand sequence read and the particular position in the distinct, yet related second strand sequence read is in agreement.

2. The method of claim 1, wherein nucleotide bases that are in agreement between the first strand sequence read and the distinct, yet related second strand sequence read are not present in a reference sequence, and wherein said nucleotide bases are identified as a true variant.

3. The method of claim 1, wherein a nucleotide base that is not in agreement between the first strand sequence read and the distinct, yet related second strand sequence read is identified as a potential artifact.

4. The method of claim 1, wherein prior to sequencing, the method further comprises amplifying each original strand of the adapter-DNA molecules, resulting in a set of copies of the original first strand of each adapter-DNA molecule and a set of copies of the original second strand of each adapter-DNA molecule, and wherein the sequencing step further comprises sequencing the set of copies of the original first strand and the set of copies of the original second strand to generate a set of first strand sequence reads and a set of distinct, yet related second strand sequence reads.

5. The method of claim 4, wherein a nucleotide base is not in agreement between the first strand sequence read and the distinct, yet related second strand sequence read, and wherein the method further comprises identifying the internal consistency of base calls among the set of sequence reads derived from each single original strand, and wherein
 a non-consistent nucleotide base is characterized as (i) a processing error if the base call is not consistent among the set of sequence reads derived from the single original strand, and
 the non-consistent nucleotide base is characterized as (ii) a site of DNA damage if the base call is consistent among the set of sequence reads derived from the single original strand.

6. The method of claim 1, wherein prior to comparing the first strand sequence read and the second strand sequence read, the method comprises associating the first strand sequence read with the second strand sequence read using one or more of an adapter sequence, sequence read length, and original strand information.

7. The method of claim 1, further comprising identifying a mutation occurring at a particular position or region in the consensus sequence as a true mutation.

8. The method of claim 1, wherein the sample is or comprises double-stranded DNA fragments from a cancer tissue, healthy tissue, or a combination thereof.

9. The method of claim 1, wherein the plurality of double-stranded adapter-DNA molecules comprise a nucleotide sequence asymmetry such that the original second strand generates the distinct, yet related second strand sequence read when compared to the first strand sequence read.

10. The method of claim 1, wherein the adapter molecules further comprise a nucleotide sequence that differentiates each original strand relative to its original complementary strand.

11. The method of claim 1, further comprising comparing the consensus sequence with a reference sequence and identifying a variant occurring at a particular position in the consensus sequence.

12. The method of claim 11, further comprising identifying the double-stranded DNA fragments as being derived from a neoplastic cell by the variant.

13. The method of claim 1, further comprising aligning the consensus sequence with a reference sequence and identifying a nucleotide sequence occurring at a particular position or region in the consensus sequence as a true nucleotide sequence.

14. The method of claim 1, wherein the plurality of double-stranded DNA fragments are circulating nucleic acid molecules.

15. The method of claim 14, wherein the circulating nucleic acid molecules comprise nucleic acid-based biomarkers from serum or plasma.

16. The method of claim 1, wherein the sample is a biological sample from a subject, and wherein the method further comprises detecting a cancer, a cancer risk, a cancer metabolic state, or a mutator phenotype in the subject by detecting a cancer-associated nucleic acid-based serum biomarker in the subject.

17. The method of claim 1, wherein the sample comprises a blood sample or a tissue sample from a subject.

18. A method of sequencing DNA comprising:
 ligating adapter molecules comprising a region of non-complementarity to a plurality of target double-stranded DNA fragments to generate a plurality of double-stranded adapter-DNA molecules;
 amplifying an original first strand and an original second strand of at least some of the double-stranded adapter-DNA molecules, resulting in a set of copies of the original first strand and a set of copies of the original second strand;
 for the at least some of the adapter-DNA molecules:
  sequencing the set of copies of the original first strand and the set of copies of the original second strand to generate a set of first strand sequence reads and a set of second strand sequence reads that are distinguishable from the set of first strand sequence reads by the region of non-complementarity; and
  confirming the presence of at least one sequence read derived from each of the original first strand and the original second strand of the adapter-DNA molecule;
  comparing the first strand sequence read with the second strand sequence read; and
  generating a consensus sequence of the target double-stranded DNA fragment wherein each position in the consensus sequence is identified as correct if the particular position in the first strand sequence read and the second strand sequence read is in agreement.

19. The method of claim 18, wherein prior to amplifying an original first strand and an original second strand of at least some of the double-stranded adapter-DNA molecules, the method further comprises selectively enriching the double-stranded adapter-DNA molecules to generate a subset of double-stranded adapter-DNA molecules for sequencing.

20. The method of claim 19, wherein selectively enriching the adapter-DNA molecules comprises selecting the adapter-DNA molecules based on a strand size.

21. The method of claim 19, wherein selectively enriching the adapter-DNA molecules occurs via primer extension capture or target DNA amplification.

22. The method of claim 19, wherein selectively enriching the adapter-DNA molecules comprises amplification of select adapter-DNA molecules with one or more primers specific to each genetic locus in a set of genetic loci among a larger set of genetic sequences in a sample.

23. The method of claim 18, wherein prior to ligating adapter molecules to the plurality of target double-stranded DNA fragments, the method further comprises selectively enriching target double-stranded DNA fragments by size selection.

24. The method of claim 18, further comprising comparing the consensus sequence to a reference sequence and identifying a variant occurring at a particular position in the consensus sequence.

25. The method of claim 24, further comprising identifying the target double-stranded DNA fragments as being derived from a neoplastic cell by the variant.

26. The method of claim 24, wherein the plurality of target double-stranded DNA fragments are circulating nucleic acid molecules.

27. The method of claim 18, wherein the target double-stranded DNA fragments comprise nucleic acid-based biomarkers from serum or plasma.

28. The method of claim 18, wherein the target double-stranded DNA fragments are derived from a biological sample comprising a blood sample or a tissue sample from a subject, and wherein the method further comprises detecting a cancer, a cancer risk, a cancer metabolic state, or a mutator phenotype in the subject by detecting a cancer-associated nucleic acid-based biomarker in the subject.

29. The method of claim 18, wherein the adapters comprise one or more single molecule identifiers (SMIs) having a degenerate or semi-degenerate sequence.

30. The method of claim 29, wherein the degenerate or semi-degenerate sequence comprises 2 or more nucleotide bases.

31. The method of claim 29, wherein each adapter comprises an SMI in at least one of a double-stranded portion or a single-stranded portion of the adapter.

32. The method of claim 18, wherein after amplifying an original first strand and an original second strand of at least some of the double-stranded adapter-DNA molecules, the method further comprises selectively enriching the double-stranded adapter-DNA molecules to generate a subset of double-stranded adapter-DNA molecules for sequencing.

33. The method of claim 32, wherein selectively enriching the double-stranded adapter-DNA molecules comprises annealing adapter-DNA strands having a desired DNA sequence by targeted hybridization to oligonucleotides with complementarity to the desired DNA sequence.

34. The method of claim 32, wherein selectively enriching the adapter-DNA molecules comprises providing an array of capture probes, wherein a plurality of the probes in the array each hybridizes to a DNA sequence that maps to a genetic locus in the reference genome.

\* \* \* \* \*

UNITED STATES PATENT AND TRADEMARK OFFICE
CERTIFICATE OF CORRECTION

PATENT NO. : 12,258,629 B2
APPLICATION NO. : 16/503398
DATED : March 25, 2025
INVENTOR(S) : Jesse Salk et al.

It is certified that error appears in the above-identified patent and that said Letters Patent is hereby corrected as shown below:

In the Claims

Claim 18, Column 40, Lines 15-19, please delete:
"amplifying an original first strand and an original second strand of at least some of the double-stranded adapter-DNA molecules,resulting in a set of copies of the original first strand and a set of copies of the original second strand;"
And replace with:
--for at least some of the double-stranded adapter-DNA molecules, amplifying an original first strand of a double-stranded adapter-DNA molecule and an original second strand of the same double-stranded adapter-DNA molecule, resulting in a set of copies of the original first strand and a set of copies of the original second strand;--

Claim 18, Column 40, Lines 32-36, please delete:
"generating a consensus sequence of the target double-stranded DNA fragment wherein each position in the consensus sequence is identified as correct if the particular position in the first strand sequence read and the second strand sequence read is in agreement."
And replace with:
--generating a consensus sequence of the first strand sequence read and the second strand sequence read of the target double-stranded DNA fragment wherein each position in the consensus sequence is identified as correct if the particular position in the first strand sequence read and the second strand sequence read is in agreement.--

Signed and Sealed this
Twenty-second Day of July, 2025

Coke Morgan Stewart
*Acting Director of the United States Patent and Trademark Office*

```
                              SEQUENCE LISTING

<160> NUMBER OF SEQ ID NOS: 9

<210> SEQ ID NO 1
<211> LENGTH: 58
<212> TYPE: DNA
<213> ORGANISM: Artificial Sequence
<220> FEATURE:
<223> OTHER INFORMATION: Synthetic oligonucleotide

<400> SEQUENCE: 1
aatgatacgg cgaccaccga gatctacact ctttccctac acgacgctct tccgatct          58

<210> SEQ ID NO 2
<211> LENGTH: 50
<212> TYPE: DNA
<213> ORGANISM: Artificial Sequence
<220> FEATURE:
<223> OTHER INFORMATION: Synthetic oligonucleotide
<220> FEATURE:
<221> NAME/KEY: misc_feature
<222> LOCATION: (5)..(16)
<223> OTHER INFORMATION: n is a, c, g, or t

<400> SEQUENCE: 2
actgnnnnnn nnnnnnagat cggaagagca cacgtctgaa ctccagtcac                   50

<210> SEQ ID NO 3
<211> LENGTH: 21
<212> TYPE: DNA
<213> ORGANISM: Artificial Sequence
<220> FEATURE:
<223> OTHER INFORMATION: Synthetic oligonucleotide

<400> SEQUENCE: 3
aatgatacgg cgaccaccga g                                                  21

<210> SEQ ID NO 4
<211> LENGTH: 23
<212> TYPE: DNA
<213> ORGANISM: Artificial Sequence
<220> FEATURE:
<223> OTHER INFORMATION: Synthetic oligonucleotide

<400> SEQUENCE: 4
gtgactggag ttcagacgtg tgc                                                23

<210> SEQ ID NO 5
<211> LENGTH: 53
<212> TYPE: DNA
<213> ORGANISM: Artificial Sequence
<220> FEATURE:
<223> OTHER INFORMATION: Synthetic oligonucleotide
<220> FEATURE:
<221> NAME/KEY: misc_feature
<222> LOCATION: (25)..(30)
<223> OTHER INFORMATION: position of fixed multiplexing barcode sequence
<220> FEATURE:
<221> NAME/KEY: misc_feature
<222> LOCATION: (25)..(30)
<223> OTHER INFORMATION: n is a, c, g, or t

<400> SEQUENCE: 5
caagcagaag acggcatacg agatnnnnnn gtgactggag ttcagacgtg tgc               53
```

```
<210> SEQ ID NO 6
<211> LENGTH: 5
<212> TYPE: DNA
<213> ORGANISM: Artificial Sequence
<220> FEATURE:
<223> OTHER INFORMATION: Synthetic oligonucleotide

<400> SEQUENCE: 6 cagta                                                                    5

<210> SEQ ID NO 7
<211> LENGTH: 16
<212> TYPE: DNA
<213> ORGANISM: Artificial Sequence
<220> FEATURE:
<223> OTHER INFORMATION: Synthetic oligonucleotide
<220> FEATURE:
<221> NAME/KEY: misc_feature
<222> LOCATION: (5)..(16)
<223> OTHER INFORMATION: n is a, c, g, or t

<400> SEQUENCE: 7
actgnnnnnn nnnnnn                                                       16

<210> SEQ ID NO 8
<211> LENGTH: 16
<212> TYPE: DNA
<213> ORGANISM: Artificial Sequence
<220> FEATURE:
<223> OTHER INFORMATION: Synthetic oligonucleotide
<220> FEATURE:
<221> NAME/KEY: misc_feature
<222> LOCATION: (1)..(12)
<223> OTHER INFORMATION: n is a, c, g, or t

<400> SEQUENCE: 8
nnnnnnnnnn nncagt                                                       16

<210> SEQ ID NO 9
<211> LENGTH: 17
<212> TYPE: DNA
<213> ORGANISM: Artificial Sequence
<220> FEATURE:
<223> OTHER INFORMATION: Synthetic oligonucleotide
<220> FEATURE:
<221> NAME/KEY: misc_feature
<222> LOCATION: (1)..(12)
<223> OTHER INFORMATION: n is a, c, g, or t

<400> SEQUENCE: 9
nnnnnnnnnn nncagta                                                      17
```